US009642862B2

(12) United States Patent
White

(10) Patent No.: US 9,642,862 B2
(45) Date of Patent: May 9, 2017

(54) METHODS FOR TREATING CHRONIC OR UNRESOLVABLE PAIN AND/OR INCREASING THE PAIN THRESHOLD IN A SUBJECT AND PHARMACEUTICAL COMPOSITIONS FOR USE THEREIN

(75) Inventor: Hillary D. White, S. Pomfret, VT (US)

(73) Assignee: White Mountain Pharma, Inc., New York, NY (US)

( * ) Notice: Subject to any disclaimer, the term of this patent is extended or adjusted under 35 U.S.C. 154(b) by 1342 days.

(21) Appl. No.: 13/299,232

(22) Filed: Nov. 17, 2011

(65) Prior Publication Data
US 2012/0130199 A1 May 24, 2012

Related U.S. Application Data

(60) Provisional application No. 61/534,174, filed on Sep. 13, 2011, provisional application No. 61/415,258, filed on Nov. 18, 2010.

(51) Int. Cl.
*A61K 31/5685* (2006.01)
*A61K 31/568* (2006.01)

(52) U.S. Cl.
CPC ........ *A61K 31/568* (2013.01); *A61K 31/5685* (2013.01)

(58) Field of Classification Search
CPC ............ A61K 31/5686; A61K 31/5685; A61K 31/568
USPC ................................................. 514/171, 178
See application file for complete search history.

(56) References Cited

U.S. PATENT DOCUMENTS

| 4,542,129 | A | 9/1985 | Orentreich |
|---|---|---|---|
| 5,019,395 | A | 5/1991 | Mahjour et al. |
| 5,206,008 | A | 4/1993 | Loria |
| 5,461,042 | A | 10/1995 | Loria |
| 5,656,606 | A | 8/1997 | Nargund |
| 5,676,968 | A | 10/1997 | Lipp |
| 5,709,878 | A | 1/1998 | Rosenbaum et al. |
| 5,855,905 | A * | 1/1999 | Oettel et al. ................ 424/426 |
| 5,855,920 | A | 1/1999 | Chein |
| 5,869,090 | A | 2/1999 | Rosenbaum |
| 5,935,949 | A | 8/1999 | White |
| 5,968,919 | A | 10/1999 | Samour |
| 6,132,760 | A | 10/2000 | Hedenstrom |
| 6,165,504 | A | 12/2000 | Bell |
| 6,197,830 | B1 * | 3/2001 | Frome .................... A61K 31/00 514/183 |
| 6,238,284 | B1 | 5/2001 | Dittgen et al. |
| 6,299,900 | B1 | 10/2001 | Reed |
| 6,319,913 | B1 | 11/2001 | Mak et al. |
| 6,503,894 | B1 | 1/2003 | Dudley |
| 6,579,865 | B2 | 6/2003 | Mak et al. |
| 6,743,448 | B2 | 6/2004 | Kryger |
| 6,818,226 | B2 | 11/2004 | Reed et al. |
| 6,923,983 | B2 | 8/2005 | Morgan et al. |
| 7,169,107 | B2 | 1/2007 | Jersey-Willuhn |
| 7,184,820 | B2 | 2/2007 | Jersey-Willuhn |
| 7,198,801 | B2 | 4/2007 | Carrara |
| 7,214,381 | B2 | 5/2007 | Carrara |
| 7,320,968 | B2 | 1/2008 | Gyurik |
| 7,335,379 | B2 | 2/2008 | Carrara |
| 7,404,965 | B2 | 7/2008 | Carrara |
| 7,470,433 | B2 | 12/2008 | Carrara |
| 7,608,605 | B2 | 10/2009 | Gyurik |
| 7,608,606 | B2 | 10/2009 | Gyurik |
| 7,608,607 | B2 | 10/2009 | Gyurik |
| 7,608,608 | B2 | 10/2009 | Gyurik |
| 7,608,609 | B2 | 10/2009 | Gyurik |
| 7,608,610 | B2 | 10/2009 | Gyurik |
| 7,799,769 | B2 | 9/2010 | White |
| 7,935,690 | B2 | 5/2011 | Gyurik |
| 8,063,029 | B2 | 11/2011 | Gyurik |
| 2002/0183296 | A1 | 12/2002 | Dudley et al. |
| 2003/0022877 | A1 | 1/2003 | Dudley |
| 2003/0027804 | A1 | 2/2003 | van der Hoop |
| 2003/0050292 | A1 | 3/2003 | Dudley et al. |
| 2003/0139384 | A1 | 7/2003 | Dudley |
| 2003/0175329 | A1 | 9/2003 | Azarnoff et al. |
| 2003/0232072 | A1 | 12/2003 | Dudley |
| 2004/0002482 | A1 | 1/2004 | Dudley et al. |
| 2004/0092494 | A9 | 5/2004 | Dudley |
| 2004/0115175 | A1 * | 6/2004 | Blau et al. ................ 424/93.7 |
| 2004/0198706 | A1 | 10/2004 | Carrara et al. |
| 2004/0220154 | A1 | 11/2004 | Kryger |

(Continued)

FOREIGN PATENT DOCUMENTS

WO    WO 99/24041    5/1999
WO    WO 01/39754    6/2001

(Continued)

OTHER PUBLICATIONS

Tennant. The use of Hormones for Chronic Pain. Journal of Prolotherapy Volumne 2, Issue 4, pp. 489-494, Oct. 2010.*
Takahashi et al. Inflammatory cytokines in the herniated disc of the lumbar spine. Spine, 1996 vol. 21, No. 2, pp. 218-224, abstract.*
Gallantine et al. Journal compilation 2008 Nordic Pharmacological Society Basic & Clinical Pharamcology & Toxicology, 103, pp. 419-427.*

(Continued)

Primary Examiner — Jennifer M Kim
(74) Attorney, Agent, or Firm — Loeb & Loeb LLP

(57) ABSTRACT

The invention relates to a method of reducing chronic inflammatory pain in a human subject with androgen deficiency symptoms comprising transdermally administering a pain-reducing amount of a composition comprising a bioactive androgen to the subject on a daily basis. The invention relates to a method of increasing the pain threshold of a human subject having symptoms of androgen deficiency comprising transdermally administering a composition comprising a pain threshold-increasing amount of a bioactive androgen to the subject with androgen deficiency symptoms on a daily basis. The invention may be used to treat males and females in order to alleviate chronic inflammatory pain or to raise the subject's pain threshold. The invention also relates to increasing the levels of endogenous opioid peptides in a human subject by administering an androgen composition to the subject.

61 Claims, 4 Drawing Sheets

(56) References Cited

U.S. PATENT DOCUMENTS

| | | |
|---|---|---|
| 2004/0220160 A1 | 11/2004 | Kryger |
| 2004/0223984 A1 | 11/2004 | Kryger |
| 2004/0259784 A1 | 12/2004 | White |
| 2004/0259852 A1 | 12/2004 | White et al. |
| 2005/0020552 A1 | 1/2005 | Aschkenasy et al. |
| 2005/0025833 A1 | 2/2005 | Aschkenasy et al. |
| 2005/0042268 A1 | 2/2005 | Aschkenasy et al. |
| 2005/0049233 A1 | 3/2005 | Dudley |
| 2005/0054623 A1 | 3/2005 | Dudley |
| 2005/0112181 A1 | 5/2005 | Dudley et al. |
| 2005/0113353 A1 | 5/2005 | Dudley et al. |
| 2005/0118242 A1 | 6/2005 | Dudley et al. |
| 2005/0142173 A1 | 6/2005 | Dudley |
| 2005/0152956 A1 | 7/2005 | Dudley |
| 2006/0100186 A1 | 5/2006 | White et al. |
| 2006/0211664 A1 | 9/2006 | Dudley |
| 2006/0280783 A1 | 12/2006 | Depietro et al. |
| 2007/0066532 A1 | 3/2007 | White |
| 2007/0154533 A1 | 7/2007 | Dudley |
| 2008/0058299 A1 | 3/2008 | Dudley et al. |
| 2008/0103120 A1 | 5/2008 | Gyurik |
| 2008/0261937 A1 | 10/2008 | Dudley et al. |
| 2008/0275013 A1 | 11/2008 | Gyurik |
| 2008/0317844 A1 | 12/2008 | Dudley et al. |
| 2009/0192131 A1 | 7/2009 | Gyurik |
| 2009/0192132 A1 | 7/2009 | Gyurik |
| 2009/0215852 A1 | 8/2009 | Bascomb |
| 2009/0318398 A1 | 12/2009 | Dudley et al. |
| 2010/0081640 A1 | 4/2010 | Gyurik |
| 2010/0216880 A1 | 8/2010 | Carrara et al. |
| 2010/0322884 A1* | 12/2010 | DiPietro et al. ............... 424/68 |
| 2011/0009318 A1 | 1/2011 | White et al. |
| 2011/0118227 A1 | 5/2011 | White et al. |
| 2011/0172196 A1 | 7/2011 | Dudley |
| 2011/0195114 A1 | 8/2011 | Carrara |
| 2011/0201586 A1 | 8/2011 | Dudley |
| 2011/0245215 A1 | 10/2011 | Carrara |
| 2011/0251167 A1 | 10/2011 | Dudley |
| 2011/0257141 A1 | 10/2011 | Carrara |
| 2011/0306582 A1 | 12/2011 | Dudley |
| 2012/0058981 A1 | 3/2012 | Dudley |
| 2012/0065180 A1 | 3/2012 | Dudley |

FOREIGN PATENT DOCUMENTS

| | | |
|---|---|---|
| WO | WO 02/17926 | 3/2002 |
| WO | WO 02/17927 | 3/2002 |
| WO | WO 02/17967 | 3/2002 |
| WO | WO 02/089849 | 11/2002 |
| WO | WO 03/002123 | 1/2003 |
| WO | WO 03/011301 | 2/2003 |
| WO | WO 03/028667 | 4/2003 |
| WO | WO 2004/037173 | 5/2004 |
| WO | WO 2004/080413 | 9/2004 |
| WO | WO 2004/091631 | 10/2004 |
| WO | 2005000236 A2 | 1/2005 |
| WO | 2005034858 A2 | 4/2005 |
| WO | 2008118423 A1 | 10/2008 |

OTHER PUBLICATIONS

WO 2005/034858 Search Report, Apr. 21, 2005, Hillary D. White.
WO 2005/000236 Search Report, Jan. 6, 2005, Hillary D. White.
Multon et al., Lack of estrogen increases pain in the trigeminal formalin model: a behavioural and immunocytochemical study of transgenic ArKO mice, Pain 114: 257-265 (2005).
Warner et al., Dehydroeplanrosterone sulphate interferes with the Abbott Architect direct immunoassay for testosterone, Ann. Clin Biochem. 43: 196-199 (2006).
Mease et al., Fibromyaigia Syndrome, J. Rheumatol. 32(11): 2270-2277 (2005).
Richman et al., Low-dose estrogen therapy for prevention of osteoporosis: working our way back to monotherapy, Menopause 13(1): 148-155 (2006).
Melzack et al., Pain Mechanism: A New Theory, Science 150(3699): 971-979 (1965).
Search Report from European Patent Application No. 08154166.6-1216 (Aug. 31, 2009).
Regnier et al. 87(7) J. Clin. Endocrin. Metab. 3074 (2002).
Dictionary Definition of "Stabilizer" Academic Press Dictionary of Science and Technology from Elsevier Science and Technology 1992, 1996 by Academic Press.
Aloisi AM, Ceccarelli I, Fiorenzani P 2003 Gonadectomy affects hormonal and behavioral responses to repetitive nociceptive stimulation in male rats. Ann N Y Acad Sci 1007:232-7.
Aloisi AM, Ceccarelli I, Fiorenzani P, De Padova AM, Massafra C 2004 Testosterone affects formalin-induced responses differently in male and female rats. Neurosci Lett 361:262-4.
Bachmann G, Bancroft J, Braunstein G, et al. 2002 Female androgen insufficiency: the Princeton consensus statement on definition, classification, and assessment. Fertil Steril 77:660-5.
Beatty WW, Fessler RG 1977 Gonadectomy and sensitivity to electric shock in the rat. Physiol Behav 19:1-6.
Cathey MA, Wolfe F, Kleinheksel SM, Hawley DJ 1986 Scocioeconomic impact of fibrositis. A study of 81 patients with primary fibrositis. American Journal of Medicine. 81:78-84.
FDA 2003 Meeting of the Arthritis Advisory Committee transcript Jun. 23, 2003. Center for Drug Evaluation and Research (www.fda.gov/ohrms/dockets/ac/cder03.html#Arthritis).
Fields HL, Basbaum AI 1994 Central nervous system mechanisms of pain modulation. In: Wall PD, Melzack R (eds) Textbook of Pain. Oxford Churchill Livingstone Press, New York, pp. 243-257.
Gaumond I, Arsenault P, Marchand S 2002 The role of sex hormones on formalin-induced nociceptive responses. Brain Res 958:139-45.
Gaumond I, Arsenault P, Marchand S 2005 Specificity of female and male sex hormones on excitatory and inhibitory phases of formalin-induced nociceptive responses. Brain Res 1052: 105-11.
Groopman J 2000 Annals of medicine: Hurting all over. Nov. 13 issue New Yorker, pp. 78-92.
Heald AH, Butterworth A, Kane JW, et al. 2006 Investigation into possible causes of interference in serum testosterone measurement in women. Ann Clin Biochem 43:189-95.
Jaszmann LJB 1976 Epidemiology of the climacteric syndrome. In: Campbell S (ed) The Management of the Menopause and Post-menopausal Years. University Park Press, Baltimore, pp. 11-23.
Kam K, Park Y, Cheon M, Son GH, Kim K, Ryu K 2000 Effects of immobilization stress on estrogen-induced surges of luteinizing hormone and prolactin in ovariectomized rats. Endocrine 12:279-87.
Liu Z, Welin M, Bragee B, Nyberg F 2000 A high-recovery extraction procedure for quantitative analysis of substance P and opioid peptides in human cerebrospinal fluid. Peptides 21:853-60.
McCain GA 1994 Fibromyalgia and myofascial pain syndromes. In: Wall PD, Melzack R (eds) Textbook of Pain, Third edition ed. Churchill Livingstone, New York, pp. 475-493.
McEwen BS 2002 "The End of Stress as We Know It". Joseph Henry Press, Washington, DC; pp. 55-66 & 107-134.
Melzack R 1999 From the gate to the neuromatrix. Pain. Suppl:S121-6.
Mendell LM 1966 Physiological properties of unmyelinated fiber projection to the spinal cord. Experimental Neurology. 16:316-32.
Moore LB, Goodwin B, Jones SA, et al. 2000 St. John's wort induces hepatic drug metabolism through activation of the pregnane X receptor. Proceedings of the National Academy of Sciences of the United States of America. 97:7500-7502.
Nayebi AR, Ahmadiani A 1999 Involvement of the spinal serotonergic system in analgesia produced by castration. Pharmacol Biochem Behav 64:467-71.
O'Malley PG, Bladen E, Tomkins G, Santoro J, Kroenke K, Jackson JL 2000 Treatment of fibromyalgia with antidepressants: a meta-analysis. J Gen Intern Med 15:659-66.
Pardridge WM, Mietus LJ, Frumar AM, Davidson BJ, Judd HL 1980 Effects of human serum on transport of testosterone and estradiol into rat brain. Am J Physiol 239:E103-8.

(56) References Cited

OTHER PUBLICATIONS

Pongratz DE, Sievers M 2000 Fibromyalgia-symptom or diagnosis: a definition of the position. Scandinavian Journal of Rheumatology—Supplement. 113:3-7.
Russell IJ 1998 Advances in fibromyalgia: possible role for central neurochemicals. Am J Med Sci 315:377-84.
Russell IJ, Orr MD, Littman B, et al. 1994 Elevated cerebrospinal fluid levels of substance P in patients with the fibromyalgia syndrome. Arthritis & Rheumatism. 37:1593-601.
Sands R, studd J 1995 Exogenous androgens in postmenopausal women. American Journal of Medicine. 98:76S-79S.
Sternberg WF, Mogil JS, Kest B, et al. 1995 Neonatal testosterone exposure influences neurochemistry of non-opioid swim stress-induced analgesia in adult mice. Pain 63:321-6.
Tsuchiya T, Nakayama Y, Sato A 1992 Somatic afferent regulation of plasma luteinizing hormone and testosterone in anesthetized rats. Jpn J Physiol 42:539-47.
Tsuchiya T, Nakayama Y, Sato A 1992 Somatic afferent stimulation-plasma corticosterone, luteinizing hormone (LH), and testosterone responses in aged male rats under anesthetization. Jpn J Physiol 42:793-804.
Vaeroy H, Helle R, Forre O, Kass E, Terenius L 1988 Elevated CSF levels of substance P and high incidence of Raynaud phenomenon in patients with fibromyalgia: new features for diagnosis. Pain. 32:21-6.
Vaeroy H, Nyberg F, Terenius L 1991 no. evidence for endorphin deficiency in fibromyalgia following investigation of cerebrospinal fluid (CSF) dynorphin A and Met-enkephalin-Arg6-Phe7. Pain 46:139-43.
Waxman J, Zatzkis SM 1986 Fibromyalgia and menopause. Examination of the relationship. Postgraduate Medicine. 80:165-167.
Woolf CJ, Thompson SW 1991 The induction and maintenance of central sensitization is dependent on N-methyl-D-aspartic acid receptor activation; implications for the treatment of post-injury pain hypersensitivity states. Pain. 44:293-9.
Yen SS 1999 Chronic anovulation caused by peripheral endocrine disorders. In: Yen SS, Jaffe RB, Barbieri RL (eds) Reproductive Endocrinology. W.B. Saunders Company, Philadelphia, pp. 479-515.
Yunus MB 1992 Towards a model of phatophysiology of fibromyalgia: aberrant central pain mechanisms with peripheral modulation. Journal of Rheumatology, 19:846-50.
Yunus MB, Inanici F 2002 Fibromyalgia syndrome: Clinical features, diagnosis, and biopathophysiologic mechanisms. In: Rachlin ES, Rachlin IS (eds) Myofascial pain and fibromyalgia, Second ediction ed. Mosby Elsevier Science, St. Louis, pp. 3-31.
Balthazart, J. et al., Effects of Clamodulin on Aromatase Activity in the Preoptic Area, Journal of Neuroendocrinology, 2005, vol. 17, 664-671.
Balthazart, J. et al., Interactions Between Kinases and Phosphates in the Rapid Control of Brain Aromatase, Journal of Neuroendocrinology, 2005, vol. 17, 553-559.
Anderberg, Ulla Maria et al., Elevated plasma levels of neuropeptide Y in female fibromyalgia patients, European Journal of Pain (1999) 3: 19-30.
Franke, Werner W., et al., Hormonal doping and androgenization of athletes: a secret program of the German Democratic Republic government, Clinical Chemistry, 43:7, 1262-1279 (1997).
Gracely, Richard H. et al., Functional Magnetic Resonance Imaging Evidence of Augmented Pain Processing in Fibromyalgia, Arthritis & Rheumatism, vol. 46, No. 5, May 2002, pp. 1333-1343.
Wolfe, Frederick, et al., The Prevalence and Characteristics of Fibromyalgia in the General Population, Arthritis & Rheumatism, vol. 38, No. 1, Jan. 1995, pp. 19-28, 1995.
Office Action of U.S. Appl. No. 10/464,310 dated May 23, 2005.
Office Action of U.S. Appl. No. 10/464,310 dated Nov. 7, 2005.
Office Action of U.S. Appl. No. 11/555,882 dated Apr. 3, 2009.
Office Action of U.S. Appl. No. 10/677,673 dated May 9, 2006.
Office Action of U.S. Appl. No. 10/677,673 dated Oct. 3, 2006.
Office Action of U.S. Appl. No. 10/677,673 dated Nov. 3, 2005.
Tamburic, Slobodanka et al., An investigation into the rheological, dielectric and mucoadhesive properties of poly (acrylic acid) gel systems, Journal of Controlled Release 37 (1995) 59-68.
Leichtnam Marie-Laure et al., Identification of penetration enhancers for testosterone transdermal delivery from spray formulations, Journal of Controlled Release 113 (2006) 57-62.
U.S. Appl. No. 78/146,691 TESS Search Results CPE-215 Filed Jul. 23, 2002.
U.S. Appl. No. 76/006,648 TESS Search Results CPE-215 File Mar. 22, 2000.
Bentley Pharmaceuticals Announces License Agreement for its Topical Testosterone Gel Formulation; License is First for CPE-215 Permeation Technology Dec. 18, 2000.
Bentley Pharmaceuticals Announces Research and Licensing Agreements for Its Topical Testosterone Gel Formulation, Business Wire Jun. 6, 2000.
Osborne, David W. et al., Skin Penetration Enhancers Cited in the Technical Literature, Pharmaceutical Technology 21(11) (1997) 58-66 (5 pages).
Moser, Katrin et al., Passive skin penetration enhancement and its quantification in vitro, European Journal of Phamaceutics and Biopharmaceutics 52 (2001) 103-112.
Karande, Pankaj et al., High Throughput Screening of Transdermal Formulations, Phamaceutical Research, vol. 19, No. 5, May 2002 655-660.
AndroGel (testosterone gel) 1%, Full Prescribing Information, 500122/500127 Rev. Dec. 2007.
Cutter, Christopher B., Compounded Percutaneous Testosterone Gel: Use and Effects in Hypogonadal Men, JABFP, vol. 14, No. 1, Jan.-Feb. 2001, p. 22-32.
Wang, Christina et al., Transdermal Testosterone Gel Improves Sexual Function, Mood, Muscle Strength, and Body Composition Parameters in Hypogonadal Men, The Journal of Clinical Endocronology & Metabolism, vol. 85, No. 8, 2000 2389-2853.
Wang, Christina et al., Pharmacokinetics of Transdermal Testosterone Gel in Hypogonadal Men: Application of Gel at One Site v. Four Sites: A General Clinical Research Center Study, J. of Clin. Endocrinol. & Metab/, vol. 85, No. 3, 2000 964-969.
Bentley Pharmaceuticals Form S-3 Registration Statement Under the Securities Act of 1933, Bentley Pharmaceuticals, Inc., Feb. 15, 2002 pp. 31-36.
Coderre, Terence J. et al., Contribution of central neuroplasticity to pathological pain: review of clinical and experimental evidence, Pain, 52 (1993) pp. 259-285.
Abe-Dohmae et al., Sumiko et al., Neurotransmitter-Mediated Regulation of Brain Aromatase: Protein Kinase C- and G-Dependent Induction, Journal of Neurochemistry, vol. 67, No. 5, 1996, pp. 2087-2095.
McEwen, Bruce S., Neural Gonadal Steroid Actions, Science, vol. 211, Mar. 20, 1981, pp. 1303-1311.
MacLusky, Neil J. et al., Sexual Differentation of the Central Nervous System, Science, vol. 211, Mar. 20, 1981, pp. 1294-1303.
Fillingim, R.B. et al., Sex-related hormonal influences on pain and analgesic responses, Neuroscience and Biobehavioral Reviews 24 (2000) pp. 485-501.
Costigan, Michael et al., Pain: Molecular Mechanisms, The Journal of Pain, vol. 1, No. 3 (Fall), Suppl 1, 2000, pp. 35-44.
Opstad, Per Kristian, Androgenic Hormones during Prolonged Physical Stress, Sleep, and Energy Deficiency, Journal of Clinical Endocrinology and Metabolism, vol. 74, No. 5, 1992, pp. 1176-1183.
Amini, Hossein, et al., Increase in testosterone metabolilsm in the rat central nervous system by formalin-induced tonic pain, Pharmacology, Biochemistry and Behavior 74 (2002), pp. 199-204.
Anonymous, "Testosterone-Topical Fortigel-Cellegy", Biodrugs 2003 17(4):299-300.
Alberti et al., "Pharmaceutical development and clinical effectiveness of a novel gel technology for transdermal drug delivery", Expert Opin. Drug Deliv 2005 2(5):935-950.
Nathorst-Boos, et al., Percutaneous administration of testosterone gel in postmenopausal women—a pharmacological study, Gyneclogical Endocrinology 2005 20(5):243-248.

(56) References Cited

OTHER PUBLICATIONS

Davis et al., Effects of aromatase inhibition on sexual function and well-being in postmenopausal women treated with testosterone:a randomized, placebo-controlled trial, Menopause:The Journal of the North American Menopause Society 2006 13(1):37-45.

Goldstat et al., "Transdermal testosterone therapy improves well-being, mood, and sexual function in premenopausal women", Menopause:The Journal of the North American Menopause Society 2003 10(5):390-398.

Gruber et al., "Effect of percutaneous androgen replacement therapy on body composition and body weight in postmenopausal women", Maturitas 1998 29:253-259.

Massin et al., "Effects of transdermal testosterone application on the ovarian response to FSH in poor responders undergoing assisted reproduction technique—a prospective, randomized, double-blind study", Human Reproduction 2006 21(5):1204-1211.

Mazer et al., "Transdermal Testosterone for Women:A New Physiological Approach for Androgen Therapy", Obstetrical and Gynecological Survey 2003 58(7):489-500.

Mylonakis et al., "Diagnosis and Treatment of Androgen Deficiency in Human Immunodeficiency Virus-Infected Men and Women", Clinical Infectious Diseases 2001 33:857-864.

Shifren, Jan L., M.D., "The Role of Androgens in Female Sexual Dysfunction", Mayo Clin Proc 2004 79(suppl):S19-S24.

Singh et al., "Pharmacokinetics of a Testosterone Gel in Healthy Postmenopausal Women", The Journal of Clinical Endocrinology & Metabolism 2006 91:136-144.

Slater et al., "Pharmacokinetics of testosterone after percutaneous gel or buccal administration", Fertility and Sterility 2001 76(1):32-37.

Amini and Ahmadiani, "Increase in testosterone metabolism in the rat central nervous sytem by formalin-induced tonic pain", Pharmacol. Biochem. Behav. 2002 74:199-204.

Amandusson et al., Estrogen receptor-like immunoreactivity in the medullary and spinal dorsal horn.

Amandusson et al., "Colocalization of Oestrogen Receptor Immunoreactivity and Preproenkephalin mRNA Expression to Neurons in the Superficial Laminae of the Spinal and Medullary Dorsal Horn of Rats", Eur. J. Neurosci. 1996.

Amandusson et al., Estrogen-induced alterations of spinal cord enkephalin gene expression, Pain 1999.

Bammann et al., "Total and free testosterone during pregnancy", Am. J. Obstet. Gynecol. 1980 137:293-298.

Blomqvist A., "Sex Hormones and Pain:A New Role for Brain Aromatase?", Cornpar. Neurol. 2000 423:549-551.

Burckhardt et al., "The Fibromyalgia Impact Questionnaire:Development and Validation", J. Rheumatol.

Crofford et al., "Fibromyalgia:Where Are We a Decade After the American College of Rheumatology Classification Were Developed", Arthr. Rheumat. 2002 46(5):1136-1138.

Dessein et al., "Hyposecretion of adrenal androgens and the relation of serum adrenal steroids, serotonin and insulin-like growth factor-1 to clinical features in women with fibromyalgia", Pain 1999 83:313-319.

Evrard et al. "Localization and Controls of Aromatase in the Quail Spinal Cord", J. Compar. Neurol. 2000.

Fletcher et al., "Failure of Estrogen Plus Progestin Therapy for Prevention", J. Amer. Med. Assoc. 2002.

Gintzler A.R., "Endorphin-Mediated Increases in Pain Threshold during Pregnancy", Science 1980 210 (Issue.

Goldenberg et al., "A Randomized, Double-Blind Crossover Trial of Fluoxetine and Amitriptyline in the Treatment of Fibromyalgia", Arthrit. Rheumat. 1996 39(11):1852-1859.

Javanbakht et al., "Pharmacokineetics of a Novel Testosterone Matrix Transdermal System in Healthy, Premenopausal Women and Women Infected with the Human Immunodeficiency Virus", J. Clin. Endocrinol. Metab. 2000.

Ma et al., "Substance P and Enkephalin Immunoreactivities in Axonal Boutons Presynaptic to Physiologically Identified Dorsal Horn Neurons. An Ultrastructural Multiple-Labelling Study in the Cat", Neuroscience 1997.

Miller et al., "Transdermal Testosterone Administration in Women with Acquired Immunodeficiency Syndrome Wasting: A Pilot Study", J. Clin. Endocrinol. Metab. 1998 83(8):2717-.

Okun et al., Beneficial effects of Testosterone Replacement for the Nonmotor Symptoms of Parkinson.

Paiva et al., "Impaired Growth Hormone Secretion in Fibromyalgia Pateints", Arthr. Rheumat. 2002.

Tapanainem et al., "Effects of growth hormone administration on human ovarian function and steroidogenic gene expression in granulosa-luteal cells", Fertility and Sterility 58(4):726-732.

Wolfe, F. et al., "The American College of Rheumatology 1990 Criteria for the Classification of Fibromyalgia".

Baldelli et al., "Growth Hormone Secretagogues as Diagnostic Tools in Disease States", Endocrine 2001 14(1):95-99.

Nampiaparampil et al., "A Review of Fibromyalgia," The American Journal of Managed Care, 10(11): 794-800 (Nov. 2004).

Hickok et al., "A Comparison of Esterified Estrogens With and Without Methyltestosterone: Effects on Endometrial Histology and Serum Lipoproteins in Postmenopausal Women." Obstetrics & Gynecology, 82(6): 919-924 (1993.

Mannerkorpi et al., "Tests of Functional Limitaions in Fibromyalgia Syndrome: A Reliability Study," Arthritis Care and Research, 12(3): 193-199 (1999).

Ho et al., "Serum sex hormone levels in pre-and postmenopausal breast cancer patients," Singapore Med. J. 50(5): 513-518 2009.

Pall et al., "Testosterone and Bioavailable Testosterone Help to Distinguish between Mild Cushing's Syndrome and Polycystic Ovarian Syndrome," Hormone and Metabolic Research 40: 813-818 2008.

Panay et al., "Testosterone treatment of HSDD in naturally menopausal women: the ADORE study," Climacteric 13: 121-131 2010.

Schover, "Androgen tehrapy for loss of desire in women: is the benefit worth the breast cancer risk?" Fertility and Sterility 90(1): 129-140 2008.

Jacobeit et al., "Safety aspects of 36 months of administration of long-acting intramuscular testosterone undecanoate for treatment of female-to-male transgender individuals," Eur. J. Endocrinol. 161: 795-798.

van de Weijer, "Risks of hormone therapy in the 50-59 year age group," Maturitas 60: 59-64 2008.

Gooren et al., "Review of Studies of Androgen Treatment of Female-to-Male Transsexuals: Effects and Risks of Administration of Androgens to Females," J. Sci. Med.5: 765-776 2008.

The North American Menopause Society, "The role of testosterone therapy in postmenopausal women: position statement of the North American Menopausal Society," Menopause 12(5): 497-511 2005.

Karrer-Voegeli et al., "Androgen Dependence of Hirsutism, Acne, and Alopecia in Women," Medicine 88(1): 32-45 2009.

Melnikova, "Pain market", News & Analysis, 589-590 2010.

Thompson, "Opioid peptides", British Medical Journal, 259-261 1984.

Budai, et al., "Endogenous Opioid Peptides Acting at u-Opioid Receptors in the Dorsal Horn Contribute to Midbrain Modulation of Spinal Nociceptive Neurons", The American Physiological Society, 677-687 1998.

Mao, "Opioid-induced Abnormal Pain Sensitivity", Current Pain and Headache Reports, 67-70 2006.

Millan, "Descending control of pain", Pergamon, progress in Neurobiology, 355-474 2002.

Selye, "Forty years of stress research: principal remaining problems and misconceptions", CMA Journal, 53-56 1976.

Zachariou, et al., "Dynorphin-(1-8) inhibits the release of substance P-like immunoreactivity in the spinal cord of rats following a noxious mechanical stimulus", European Journal of Pharmacology, 159-165 1997.

Foldes, "Pain Control with Intrathecally and Peridurally Administered Opioids and other Drugs", Anaesthesiol. Reanimat, 287-298 1991.

(56) References Cited

OTHER PUBLICATIONS

Siemion, et al., "The peptide molecular links between the central nervous and the immune systems", Amino Acids, 161-176 2005.
Abs, et al., "Endocrine Consequences of Long-Term Intrathecal Administraton of Opioids", The Journal of Clinical Endocrinology & Metabolism, 2215-2222 2000.
Long, et al., "Blood-Brain Barrier: Endogenous Modulation by Adrenal-Cortical Function", Science, 1580-1583 1985.
Liu, et al., "A high-recovery extraction procedure for quantitative analysis of substance P and opioid peptides in human cerebrospinal fluid",Peptides, 853-860 1999.
Bellinger, et al., "Remodeling of ryanodine receptor complex causes "leaky" channels: A molecular mechanism for decreased exercise capacity", PNAS, 2198-2202 2008.
Selye, "Stress and the General Adaptation Syndrome", British Medical Journal, 1383-1392 1950.
Selye, et al., "Adaptive Reaction to Stress", Institute of Experimental Medicine and Surgery, University of Montreal, 149-157 1950.
Selye, "Interactions Between Systemic and Local Stress", British Medical Journal, 1167-1170 1954.
Selye, "To the editor", University of Montreal, 718 1976.
Sapolsky, et al., "How Do Glucocorticoids Influence Stress Responses? Integrating Permissive, Suppressive, Stimulatory, and Preparative Actions", Endocrine Reviews, 55-89 2000.
Holman, "Dopamine: From Parkinson's Disease to Fibromyalgia", Fibromyalgia Frontiers, 1-6 2005.
Sances, et al., "Course of migraine during pregnancy and postpartum: a prospective study", Cephalagia, 197-205 2003.
Daniell, et al., "Open-Label Pilot Study of Testosterone Patch Therapy in Men With Opioid-Induced Androgen Deficiency", The Journal of Pain, 200-210 2006.
Daniell, "DHEAS Deficiency During Consumption of Sustained-action Prescribed Opioids: Evidence for Opioid-Induced Inhibition of Adrenal Androgen Production", The Journal of Pain, 901-907 2006.
Daniell, "Opioid-induced androgen deficiency", Lippincott Williams & Wilkins, 262-266 2006.
Daniell, "Opiod-induced Androgen Deficiency Discussion in Opioid Contracts", The American Journal of Medicine, 120 2007.
Hsiung, "The Virtual En-psych-lopedia by Dr. Bob", DSM-IV Diagnoses and Codes, Numerical Listing, 1-16 2008.
Faubel, "Testosterone Deficiency in Chronic Pain Patients Taking Opioids", Articles of The Pain Source, 1-2 2010.
Stoffel, et al, "Gonadal Hormone Modulation of Mu, Kappa, and Delta Opioid Antinociception in Male and Female Rats", Department of Psychology, Washington State University, 1-24 2005.
Felig, et al., "Endocrinology and Metabolism", 1-10 2001.
Forman, et al., "The Response to Analgesia Testing Is Affected by Gonadal Sterioids in the Rat", Life Sciences, 447-454 1989.
Gruber, et al., "Effect of percutaneous androgen replacement therapy on body composition and body weight in postmenopausal women", Maturitas, Journal of the Climacteric & Postmenopause, 253-259 1998.
Holaday, et al., "Adrenal Steroids Indirectly Modulate Morphine and B-Endorphin Effects", The Journal of Pharmacology and Experimental Therapeutics, 176-183 1978.
Katz, et al., "The Impact of Opioids on the Endocrine System", Clin/Pain, 170-175 2009.
Leposavic, et al., "Age-Associated Remodeling of Thymopoiesis: Role for Gonadal Hormones and Catecholamines", NeuroImmunoModulation, 290-322 2008.

Munoz-Cruz S., et al., "Non-Reproductive Effects of Sex Sterioids: Their Immunoregulatory Role", PubMed, 2011.
Pednekar, et al., "Role of Testosterone on Pain Threshold in Rats", Indian J Physiol Pharmacol, 423-424 1995.
Perisic, et al., "Role of ovarian hormones in age-associated thymic involution revised", Immunobiology, 275-293 2010.
Gennaro, "Remington: The Science and Practice of Pharmacy: Medicated Tropicals", 836-857 1885.
Smith, et al., "Estrogen Resistance Caused by a Mutation in the Estrogen-Receptor Gene in a Man", The New England Journal of Medicine, 1056-1061 1994.
Tennant, "Testosterone Replacement in Female Chronic Pain Patients", Practical Pain Management, 23-27 2009.
Tennant, "Testosterone Replacement in Chronic Pain Patients", Practical Pain Management, 2010.
White, et al., "CD3+CD8+ Activity Within the Human Female Reproductive Tract, The American Association of Immonologists, 3017-3027 1997.
Zoller, et al., "Murine pregnancy leads to reduced proliferation of maternal thymocytes and decreased thymic emigration", Immunology, 207-215 2007.
Ansel's Pharmaceutical Dosage Forms and Delivery Eighth Edition, "Transdermal Drug Delivery Systems," (Ed. Allen et al.) (2005).
Block, LH, "Medicated Topicals," in Remington: The Science and Practice of Pharmacy, 20th Edition, ed. Alfonso R. Gennaro, et al. (Philadelphia: University of the Sciences, 2000), 836-857.
Lee W-Y T, Robinson RJ., "Controlled-Release Drug Delivery Systems," in Remington: The Science and Practice of Pharmacy, 20th Edition, ed. Alfonso R. Gennaro, et al. (Philadelphia: University of the Sciences, 2000), 917-918.
Ohlsson, et al., "The role of estrogens for male bone health," European Journal of Endocrinology, 160:883-889, Jun. 1, 2009 (Online Publication, Mar. 20, 2009).
Testim 1% (testosterone gel) Prescribing Information; Sep. 2003.
Bracken, M.B. "Why Animal Studies are often poor predictors of human reactions to exposure", J. R. Soc. Med., vol. 101:120-122, 2008.
Borzan, J. & Fuchs, P.N. "Organizational and Activational Effects of Testosterone on Carrageenan-Induced Inflammatory Pain and Morphine Analgesia", Neuroscience, vol. 143:885-893, 2006.
Faubel, C. "Testosterone Deficiency in Chronic Pain Patients Taking Opioids", The Pain Source, Sep. 8, 2010 (Online Publication).
Tennant, F. "Testosterone Replacement in Chronic Pain Patients", Practical Pain Management, 10(6):12-15, Jul./Aug. 2010.
Tennant, F. "Testosterone Replacement in Female Chronic Pain Patients", Practical Pain Management, 9 (9):25-27, Nov./Dec. 2009.
Ossipov, M.H. et al. "Induction of pain facilitation by sustained opioid exposure: relationship to opioid antinociceptive tolerance", Life Sciences, 73:783-800, 2003.
International Search Report corresponding to related PCT Application No. PCT/2004/019201 (WO2005000236); Mailed Jun. 7, 2005.
International Search Report corresponding to related PCT Application No. PCT/2004/030940 (WO2005034858); Mailed Dec. 2, 2005.
AM Aloisi and I Ceccarelli, "Role of Gonadal Hormones in Formalin-Induced Pain Responses of Male Rats: Modulation by Estradiol and Naloxone Administration" Neuroscience 95 (2):559-566, 2000.
Stoffel et al., "Gonadal Hormone Modulation of Mu, Kappa, and Delta Opioid Antinociception in Male and Female Rats", Department of Psychology, Washington State University, 1-24, 2005 (Published in final edited form as: J Pain. Apr. 2005; 6(4):261-274).

\* cited by examiner

METHODS FOR TREATING CHRONIC OR UNRESOLVABLE PAIN AND/OR INCREASING THE PAIN THRESHOLD IN A SUBJECT AND PHARMACEUTICAL COMPOSITIONS FOR USE THEREIN

This application claims priority to U.S. Provisional Patent Application No. 61/415,258, filed Nov. 18, 2010 and U.S. Provisional Patent Application No. 61/534,174, filed Sep. 13, 2011, which applications are each incorporated by reference herein in their entirety.

INTRODUCTION

The invention relates to the administration of a pain-reducing androgen to a human subject in a safe and effective way. The invention relates to a method of reducing unresolvable chronic or acute pain (hereafter called either chronic pain or pain) in a human subject with androgen deficiency symptoms (as defined elsewhere herein) comprising administering a composition comprising a pain-reducing amount of an androgen to a human subject, wherein the subject's androgen serum levels are restored to safe levels within the reference range, such that pain is reduced safely and effectively, as discussed herein. This inflammatory or chronic pain described in the instant invention is distinct and separate from fibromyalgia, as described herein.

The invention also relates to the administration of a pain-threshold-increasing androgen to a human subject in a safe and effective way in patients both with and without unresolved pain. The invention further relates to a method of increasing the pain threshold of an human subject with androgen deficiency symptoms, as defined herein, comprising administering a composition comprising a pain threshold-increasing amount of an androgen to a human subject, wherein the subject's androgen serum levels are restored to safe levels within the appropriate reference range so that the subject's pain threshold is increased safely and effectively.

The usage of androgens to treat unresolvable pain, or low threshold pain, is unique. The present invention relates to pain due to chronic inflammatory pain states, and to the formulation of treatment strategies thereof. Such chronic pain states have been seen as the focus for developing the many different treatments for chronic pain. Therefore, conceptualization of most all treatment strategies has revolved around understanding the causes of pain for each of these pain states, each being instructive as an example for the best approaches to therapy. Simply put, treatments had to be developed for each different type of chronic pain. The present invention focuses on a different approach to this population by seeing their pain as caused by a variety of biologic stressors, derived from either the environment and/or genetic predisposition, that deplete androgen levels and induce androgen deficient states. Current standard practice pain therapies for treating unresolvable pain do not include the androgen sex steroid hormone class of drugs. The same approach applies to treatment of patients with a low threshold of pain.

The androgen, as described for all embodiments of the invention, is an androgen with biologic activity, also called "bioactive androgen" or "androgen." It can be administered by a variety of means, including, but not limited to, transdermal or transmucosal administration, oral administration, time release capsule, by injection, and by suppository. The androgen can be administered on a daily basis. Alternatively, the androgen can be administered to the subject over any period of time wherein the subject's pain is alleviated and/or the subject's pain threshold increased in a safe and efficacious manner. Also the androgen can be administered over any period of time to a subject without pain, wherein the subject's pain threshold is increased in a safe and efficacious manner. Further, the androgen can be administered to increase the levels of endogenous opioid peptides in a subject.

BACKGROUND OF THE INVENTION

Current therapies for chronic or acute pain are often either ineffective and/or have substantive risks relative to the benefits. To date, it is difficult to find reliable and satisfactory methods for addressing either chronic or acute pain in patients that fail to resolve that pain in such a way that they heal and achieve a feeling of well-being. Some of the more well-known therapeutics for pain involve the usage of: 1) the non-steroidal anti-inflammatory drugs or NSAID analgesics; 2) the morphine-related opioid analgesic class of drugs, such as oxycodone and hydromorphone; and 3) the usage of anti-depressants, for example the Serotonin-Norepinephrine Reuptake Inhibitor (SNRI) and Selective Serotonin Reuptake Inhibitor (SSRI) classes of drugs including duloxetine, sertraline, venlafaxine, and fluoxetine, the tricyclic class of antidepressants; and cognitive behavioral therapy. However, all of these approaches suffer from either a lack of efficacy and/or unintended side effects that are frequently worse than the benefits. For example, the NSAID class of analgesics, when used for chronic pain over a period of time, can cause significant GI tract irritation. With respect to the opioid or morphine related class of drugs, recent data indicate that chronic usage can even be responsible for and induce pain by itself (Mao, J., "Opioid-induced Abnormal Pain Sensitivity," Current Pain and Headache Reports, 2006, 10:67-70). In addition, side effects for opiates include nausea and vomiting, confusion, compromised immune function, subnormal testosterone levels in males leading to osteoporosis, addiction, lack of efficacy over time (tolerance), and constipation. The anti-depressants are well known in the clinical realm as having sexual dysfunction side effects, including arousal disorder, ejaculation failure and difficulty achieving orgasm, as well as an FDA mandated black box warning for increased risk of suicidality. Other common side effects for anti-depressants include nausea, insomnia, dizziness, tremor, and decreased libido.

The sex steroid hormones are normally considered to be important in the clinic for sexual health, but have never been used in routine practice or as standard therapy in the clinic to reduce chronic pain. Androgens, estrogens and progestins, or their agonists and antagonists, are used by reproductive endocrinologists within the clinic to treat sexual disorders. The use of these hormones are not normally thought of outside the context of sexual function such as reproduction and secondary sex traits. However, more recently, it has been recognized that estrogens, for example, are important in the health of men for bone plate formation (Smith et al., The New England Journal of Medicine, 1994, 331:1056-1061; Ohlsson and Vandenput, European J. of Endocrinology, 2009, 160:883-889). Likewise, it is plausible that androgens are important for overall health beyond their role in reproduction. The instant invention relates to the importance of healthy serum levels of testosterone for non-reproductive neuroendocrine health for reducing pain and/or increasing pain threshold, and to foster feelings of well-being. There is also accumulating evidence that the sex hormones, in particular estrogens, progestins, and now testosterone, can be correlated to subjective feelings of well-being and quality of life. In fact, either too high or too low levels of the sex steroid hormones, including testosterone, result in a loss of feeling of well-being. Specifically, testosterone can have an effect on dopamine, serotonin, N-methyl-D-aspartic acid (NMDA), and enkephalinergics, all of which contribute to feelings of well-being and modulation of mood. The best way to evaluate testosterone deficiency in the clinic is to look for clinical symptoms of too-low androgen levels in a human subject whose blood serum levels are in the lower half of the reference range.

Clinical symptoms of androgen insufficiency may include, but are not limited to, loss of libido, bouts of impotence, chronic fatigue, insomnia, hot flushes, sweating, alopecia or hair loss, mood change, mood swings, nervousness, loss of feelings of well-being, anemia such as that caused by insufficient erythropoietin production, impaired memory, inability to concentrate, Alzheimer's Disease (patients with androgen insufficiency have a higher risk), andropause (low production of androgens), night sweats, anovulatory menstrual cycles, amenorrhea, menorrhagia, menometrorragia, metrorrhagia, oligomenorrhea, polymenorrhea, decrease in muscle mass, osteoporosis, compression fractures, and obesity (unhealthy fat to muscle ratios). In addition, disorders such as diabetes, hypertension, Klinefelter's, Wilson-Turner and Androgen insensitivity syndromes can produce hypogonadism.

Acute vs. chronic pain. Acute pain is a sensation that is normally triggered in the nervous system to alert an individual about possible injury and the need to respond to the situation. Chronic pain is different. Chronic pain, usually inflammatory in nature, has been defined by the National Institute for Neurological Disorders and Stroke as persistent pain, which can last as long as six months or more. Here, pain signals keep firing in the nervous system for weeks, months, even years. There may have been an initial mishap, such as a sprained back, or serious infection, or there may be an ongoing cause of pain, such as arthritis, cancer, or an ear infection, but the nervous system inappropriately fails to dampen and thereby resolve the painful insult. Some people suffer chronic pain in the absence of any past injury or evidence of body damage. Temporal summation of pain and "wind-up" phenomena, whereby pain is amplified in intensity over time and the painful area increases in size, are thought to be involved, although the biologic mechanisms for controlling pain remain poorly defined. Furthermore, the reasons why some people are more susceptible to pain than others has not been well understood. Many chronic pain conditions affect older adults, but they are not limited to older adults. Common chronic pain complaints include headache, low back pain, cancer pain, arthritis pain, neurogenic pain (pain resulting from damage to the peripheral nerves or to the central nervous system itself), and so-called "psychogenic" pain (pain not due to past disease or injury or any visible sign of damage inside or outside the nervous system, but to psychological trauma, for example). Here we define pain as unresolvable chronic or acute inflammatory pain, or an abnormally low pain threshold due to stress/distress on/within the individual that is unresolvable.

There are numerous conditions that are accompanied with, or caused by pain, some of which involve chronic pain. There are also numerous theories relating to the treatment of chronic pain. Presently, there is extensive ongoing research relating to pain, how pain is transmitted through and perceived by the body, and treatments to overcome, or at least alleviate pain. The importance of receptors in the body and how some neurotransmitters function is being studied (See, e.g., Millan, 2000, Prog. Neurobiol. 66:255-474), although effective treatment of pain in the clinic remains problematic.

Stress on an individual can be resolved ("eustress"), but when stress is unresolvable by the individual ("distress"), it can be the basis of unresolvable pain. It is known that chronic pain can be the result of a wide variety of stressor conditions and stressor states, including disease, surgery, various types of trauma and/or physical distress. Emotional distress such as grief, and pathologic states within the immune system, nervous system, endocrine system, and other biologic systems can also act as stressor states that contribute to pain. Such stress can lead to unresolvable pain in both females and males. Selye defines stress as a "nonspecific response of the body to any demand. A stressor is an agent that produces stress at any time." (Selye, CMA Journal, 1976, 115:53-56 at 53). Selye's "general adaptation syndrome" recognizes three phases in an individual's resistance to stress: the initial alarm, resistance to that alarm, and if not resolved, exhaustion. Further, Selye coined the term "eustress" in which the individual responds to a stressor such that adaptation and coping responses resolve the stress, as opposed to "distress" in which the individual's stress response fails to be resolved. However, it is not well understood why, despite cognitive behavior modification training, for example, some individuals are able to adapt so much better than others, or why an individual who has previously been able to adapt can no longer do so. In other words, sometimes the individual can adapt to the stress such that the stress is resolved, while in other situations the individual cannot adapt, and the stress on the individual remains unresolved. When the stress is resolved, the result is a state of eustress. When the stress is unresolvable, the result is a state of distress and a lack of feeling of well-being, resulting in pain and/or illness. Part of the problem is our poor understanding of how the various neuroendocrine and immunologic pathways modulate our responses to stress, and promote or fail to promote eustress and feelings of well-being in an individual. It is not widely appreciated that stress, by itself, can catabolize and exhaust the body's supply of androgens, as exemplified by individuals studied during combat training (Opstad, P. K., et al., J. Clinical Endocrinology & Metabolism, 1992, 74:1176-83). The instant invention here is that androgen therapy can restore healthy serum levels of androgen and thereby ameliorate distress, can partially or completely resolve that stress, and can reestablish a state of eustress along with feelings of well-being. Further, androgen therapy that restores stress-depleted androgen levels to effective and safe levels, while providing significant clinical responses without clinical evidence of androgen excess, is driven largely by effective processing and dampening of pain, the mechanism for which is clearly laid out herein. Finally, in one embodiment, the instant invention encompasses the use of androgen therapy to enable stress to be processed and pain to be decreased.

Current treatment of unresolvable inflammatory pain. Treatment for chronic inflammatory pain includes some of the same treatments for acute pain, including opioids, non-opioid analgesics, and anti-inflammatory drugs. Treatment of chronic pain can also include additional approaches, such as, antidepressants, acupuncture, local electrical stimulation, and brain stimulation, as well as surgery. Some physicians use placebos, which in some cases has resulted in a lessening or elimination of pain. Psychotherapy, relaxation, and medication therapies, biofeedback, and behavior modification may also be employed to treat chronic pain.

Sex steroid hormones, notably androgens, can be important for pain processing. There is some evidence that both androgens and estrogens play a role in pain sensation in animal models, although this has not been adequately studied or approved in humans for chronic pain. Further, it appears that gender can have an impact on the sensation of pain. It is well known, for example, that testosterone decreases the production of sex hormone binding globulin (SHBG), while estradiol increases SHBG production. SHBG acts to sequester sex steroid hormones away from the bioavailable pool, preventing entry of sex steroid hormones across the blood-brain barrier (BBB) into the central nervous system. There is evidence that the blood-brain barrier is more permeable to testosterone than estradiol; in rodents, the fetus has a SHBG-like protein, fetoneonatal estrogen binding protein (alpha-fetoprotein) that is thought to act to sequester peripheral estrogen, but not testosterone, away from the central nervous system (MacLusky et al., Science, 1981, 211:1294). In addition, the concept that SHBG can prevent entry of sex hormones through the blood-brain barrier to the central nervous system has been shown in a human-into-rodent model (Pardridge W. M. et al. The American Journal of Physiology, 1980, 239:1 E103-E108). These findings are consistent with the theory that it is testosterone rather than 17-beta estradiol that most effectively transits from serum through the blood-brain barrier and into the central nervous system to mediate anti-nociception. It is the nociceptive relay neurons in the spinal cord that are well known to be important for transmitting pain signals, and conversely they can also be involved in dampening pain.

Gonadal or sex steroid hormones down-regulate inflammatory cell responses. It is well known that there is an inverse correlation between gonadal steroid hormones (estrogens, progestins and androgens) and inflammation. First, at puberty gonadal steroid hormone serum levels surge when the thymus correspondingly undergoes "involution," in which there is decreased thymic cellularity, decreased thymic cell development, and decreased thymic cell output to the periphery as measured by recent thymic emigrants (RTE) (a good measure of peripheral thymic cells, also known as T cells or T lymphocytes, which are critical for inflammation). Second, during pregnancy, the acute surge in gonadal steroid hormone serum levels that occurs results in further thymic involution, and consequently greatly decreased numbers of peripheral thymocytes which would otherwise recognize the embryo as foreign and reject it. Concomitant with the decreased thymic T cell output in pregnancy is a high susceptibility to infection, for example the high risk of pregnant women to infection from rubella (measles), which can be abortogenic (which is in itself an inflammatory response that overcomes the mother's immunologic tolerance of the fetus, thereby rejecting it as foreign) or result in severe harm to the fetus. In fact, researchers use this increased susceptibility to infection in pregnancy to successfully infect animals with pathogens (pathogens which would otherwise be eliminated by the immune system) to create animal model systems for studying those pathogens. Third, gonadectomy (e.g., ovariectomy of animals) results in a reversal of thymic involution, restoration of thymic cellularity and thymic output, and an increased T cell repertoire (in both diversity and numbers) in the periphery (Perisic M. et al., "Role of ovarian hormones in age-associated thymic involution revisited," Immunobiology, 2010, 215(4):275-293). Fourth, rescue of gonadectomy with exogenous hormone by injection of gonadal steroid hormones into animals decreases the numbers of thymocytes and T cells in the periphery (Zoller A. L. et al., "Murine pregnancy leads to reduced proliferation of maternal thymocytes and decreased thymic emigration," Immunology, 2007 121(2):207-215).

Hormone replacement therapy in women has focused on estrogens and progestins, but not on androgens. The Women's Health Initiative (WHI) clinical trial, whose aim was to prospectively evaluate the risks and benefits of orally administered combination hormone replacement therapy in healthy women using estrogens and medroxyprogesterone acetate, was relatively recently halted (Fletcher, S. W., et al., J. Amer. Med. Assoc., 2002, 288: 366-368). The increased risks in coronary heart disease, breast cancer, stroke, and pulmonary embolism outweighed the increased benefits in colorectal cancer, endometrial cancer, hip fractures and death due to other causes, resulting in a small but statistically significant increased risk for the global index of hazard ratios among women taking these hormones. The authors pointed out, however, that their study only evaluated healthy women, not those with symptoms of hormone deficiency. This means that the treatments would have raised the serum levels of hormones to a level exceeding the normal levels of hormones for women of the same age. Furthermore, these treatments were orally administered. Other routes of delivery, e.g., transdermal systems, need to be studied, since it is possible that transdermal delivery may increase benefits and/or decrease risks to these patients. It was noted by the authors of the WHI study that hormone replacement therapy is still considered to be effective for relieving peri-menopausal symptoms such as hot flashes. Since the completion of the WHI trial, it has also been found that hormone replacement therapy has greater benefits and rare risks in women aged 50-59, a younger age group relative to the WHI trial (van de Weijer et al., Maturitas, 2008, 60:59). On Mar. 31, 2009, methyltestosterone combined with estrogens (Solvay's ESTRATEST®), prescribed to women for hot flashes when they failed to get relief from estrogen replacement therapy, was taken off the market because Solvay never demonstrated efficacy to the FDA. The FDA's new regulation system (Drug Efficacy Study and Implementation, DESI) required additional studies on ESTRATEST® to prove drug efficacy, which forced ESTRATEST® to fall under the unapproved drugs category on the FDA's DESI list.

Androgen therapy is effective against muscle wasting, for example in AIDS, but has not been approved to treat chronic inflammatory pain states. Most clinical trials evaluating sex hormone replacement therapy have focused on estrogens and progestins in women. Testosterone replacement therapy in individuals who may be testosterone deficient is now beginning to be addressed using transdermal delivery systems. For example, disease states in which there is loss of muscle mass may be treated with transdermal testosterone administration. This includes wasting syndrome in women with AIDS (Miller, K., et al., J. Clin. Endocrinol. Metab., 1998, 83:2717-2725; Javanbakht, M. et al., J. of Clinical Endocrinology & Metabolism, 2000, 85:2395-2401).

However, there is still an unmet need to develop therapeutic agents for pain that are both safe and effective, and with minimal adverse side effects, for chronic pain. In addition, there is a need to provide treatment for unresolvable chronic and acute pain that is often experienced by both females and males who are deficient in androgens, such as testosterone.

SUMMARY OF THE INVENTION

Androgens can be useful for modulating the sensation of pain and distress; thus, androgen therapy can be used to treat unresolvable chronic inflammatory pain states or their associated states of distress. The present invention relates to chronic pain states, and to the formulation of treatment strategies thereof. The basis of the invention resides in the treatment with testosterone of chronic pain due to stressor states that affect males and females, said stressor states having a significant impact on pain sensation in such patients because of causing an androgen deficient state or symptoms of androgen deficiency ("distress"). Thus, there is a need to provide treatment for chronic pain experienced by both females and males who are deficient in androgens, including testosterone, such that chronic pain or a stressor state is alleviated.

The fundamental basis or foundation of the invention here (to treat chronic inflammatory pain with androgen therapy) is the combination of these disparate observations in animals into a unifying pathway (the "Circle Hypothesis") that provides a mechanistic basis by which androgens dampen or down-modulate chronic pain in humans. FIGS. 3A-3B, described more fully herein, show the hypothesized metabolic pathway for testosterone in relation to nociception in the central nervous system. Normally, a painful stimulus or state of stress upregulates Substance P, which is, in effect, a signal for pain or stress in the CNS. Pain or stress also causes serotonin levels to drop, thus reducing feelings of well-being. Substance P, in turn, stimulates aromatase within the spinal cord nociceptive relay neurons. This Substance P regulation of aromatase is mediated by protein kinases and phosphoprotein phosphatases which can act quickly and in a complex way to allow the body to respond appropriately to pain and stress. Testosterone, as the substrate for aromatase, can cross the blood-brain barrier much more readily than estrogens (the transit of sex steroid hormones across the blood-brain barrier (BBB) is highly regulated by sex hormone binding globulin as well as aromatase enzymology), thus allowing aromatase in the spinal cord nociceptive relay neuron to convert testosterone to 17-beta estradiol within the central nervous system. Enkephalins (opioid peptides) are expressed within the spinal cord nociceptive relay neurons in response to 17-beta estradiol, resulting in the dampening of pain and the negative feed-back down-regulation of Substance P, and thereby bringing the pathway full circle back to a resting state. In patients having unresolved chronic inflammatory pain or other stressors or trauma, however, this cycle is "frustrated," and cannot progress: testosterone is exhausted and depleted in response to the unresolved chronic inflammatory pain or stressor state, resulting in a depletion of 17-beta estradiol in the spinal cord, a failure to produce opioid peptides, such as enkaphalins, and a failure to alleviate the pain/stress state. Thus, insufficient testosterone levels not only fail to allow for recovery from the initial painful stimulus or stressor, but they can also contribute to the chronic pain state and help establish a state of distress (defined elsewhere). In addition to the spinal cord, aromatase is also found in the brain and the periphery, allowing for these mechanisms to take place in both the CNS and the periphery in response to pain or stress. This Circle Hypothesis is discussed in greater detail herein.

Background on Androgens. Generally, the androgen used in the invention is a biologically active androgen. Biologically active androgens may be active in their native state, may be a precursor or pro-drug that is metabolized to a biologically active state upon ingestion by the subject. The biologically active androgen may be, but is not limited to, testosterone, androstenedione, androstendiol, dehydroepiandrosterone, danazol, fluoxymesterone, oxandrolone, nandrolone decanoate, nandrolone phenpropionate, oxymethalone, stanozolol, methandrostenolone, testolactone, pregnenolone, dihydrotestosterone, methyltestosterone, bioactive androgen precursors, or testosterone esters. Although the invention may incorporate use of any of the above (or other) androgens, testosterone is frequently discussed as an exemplary androgen compound.

Androgens bind not only to androgen receptors, but they also are able to act within cells via androgen receptor (AR) independent pathways to ameliorate and reverse the physiological consequences of low testosterone and resultant loss of feelings of well-being. The instant invention can act both at the AR level and the AR-independent level to reduce androgen deficiency symptoms. The treatments of the invention, as primary therapies, can either replace or be used in combination with other pharmacological agents. One of ordinary skill in the art, based on these teachings, would be able to discern the patients who might benefit from such a treatment and determine the effective and safe dosage for use in patients.

Androgens can modulate pain. In animal models, pain appears to be reduced during pregnancy via opiate production, when testosterone concentrations are elevated. Anecdotal evidence suggests that there is a high risk of pain symptoms in women who have undergone bilateral oophorectomy (testosterone is produced in the ovaries and adrenal glands), and conversely, symptoms appear to temporarily abate for patients during pregnancy. It is known that during pregnancy, migraine headache frequency declines and temporomandibular disorder (TMD) pain is reduced, and after pregnancy, when the sex steroid hormone levels can drop more severely than usual, feelings of well-being can be lost (Sances G. et al., Cephalagia, 2003, 23:197-205).

Androgens can improve clinical symptoms of non-inflammatory fibromyalgia patients (a counter-intuitive concept since androgens have historically been considered reproductive hormones rather than hormones that impact pain responses). The vast scientific literature on androgens and the sex steroid hormones in general relates to their ability to promote reproduction. And androgens in particular are notable for their role and abuse potential in promoting muscle strength.

White et al. (U.S. Pat. No. 5,935,949 and U.S. Pat. No. 7,799,769) previously conducted studies that provide initial proof of concept that testosterone given transdermally to female fibromyalgia patients could both significantly and safely raise serum hormone concentrations from baseline levels to levels that approximate those normally found in premenopausal women, as well as significantly improve the symptoms of non-inflammatory fibromyalgia tender point pain along with other fibromyalgia symptoms that, taken together, uniquely define this syndrome, all without inducing any of an extensive list of symptoms of androgen excess.

Neither U.S. Pat. No. 7,799,769 nor U.S. Pat. No. 5,935,949 relate to or cover the non-fibromyalgia chronic inflammatory pain states of the instant invention, as described herein. It is clear that fibromyalgia muscle tender point pain, as discussed above in the afore-mentioned patents, is distinct from most other types of pain, and that androgen hormone therapy has not been considered for reducing non-fibromyalgia, chronic inflammatory pain in the clinic or unresolved stress conditions with low pain thresholds.

Chronic inflammatory pain is clinically distinct from fibromyalgia muscle tender point pain. It is clear that chronic inflammatory pain is a distinct clinical entity from fibromyalgia-related tender point non-inflammatory pain. This conclusion is based on: 1) Diagnostic and Statistical Manual of Mental Disorders (DSM) criteria for medical diagnosis are distinctly different; 2) fibromyalgia is a diffuse illness of unknown mechanism and defined by distinctly widespread and painful tender points above and below the waist and on the right and left sides; the cause of chronic inflammatory pain is generally known and can relate to pathology of bones, nerves, and connective tissue as found, for example, in autoimmunity, cancer, infectious diseases and injury (although other stressors can induce chronic inflammatory pain); 3) erythrocyte sedimentation rate is not changed for fibromyalgia patients, but is elevated for chronic inflammatory pain states; 4) most patients with chronic inflammatory pain see a neurologist or anesthesiologist for treatment, while fibromyalgia patients generally see a rheumatologist; 5) the treatments and analgesics used for each group are generally different (chronic inflammatory pain patients are prescribed medications such as analgesics, opioids, muscle relaxants—as for lower back pain; fibromyalgia patients receive antidepressants and/or sedative for sleep, along with analgesics); 6) immobilization is often required for neurologic inflammatory pain due to injury or accident, but immobilization is discouraged for fibromyalgia patients; 7) fibromyalgia pain occurs mostly in women whereas males and females are equally at risk for chronic inflammatory pain.

Clinical testing for chronic inflammatory pain patients is distinct from that for fibromyalgia patients. Further, there are different tests that can be performed by physicians, which can also give an indication regarding the etiology of certain conditions and a way of classifying the patient's condition. For example, a laboratory test known as the erythrocyte sedimentary rate, or "sed rate," measures the rate at which a patient's red blood cells settle to the bottom of a tube or assay vessel over a prescribed period of time. This is a non-specific test that indicates the presence of an inflammatory process in a patient. Inflammatory responses are an indicator of immune system-derived mediators from white blood cells that signal pain to the nervous system. And it is the neurologist who normally treats chronic inflammatory pain states. All chronic inflammatory pain states have positive, or elevated "sed rates," confirming the inflammatory process. Fibromyalgia, on the other hand, is distinct from chronic inflammatory pain, in that fibromyalgia is a rheumatologic illness, and such patients have "sed rates" that are unchanged from "normal" sed rates. This indicates that fibromyalgia is caused by a very different process than what typifies the autoimmune or infectious disease states, for example, of chronic inflammatory pain. Further, for patients with chronic inflammatory pain, testosterone levels can be exhausted, and a low testosterone level can lead to a hyperinflammatory state, thus exacerbating the chronic inflammatory pain state. Patients exhibiting chronic inflammatory pain are likely to visit a neurologist, whereas a fibromyalgia patient is likely to see a rheumatologist. Generally, these two distinct sets of doctors are uniquely versed in different treatments. For example, a rheumatologist who sees a large number of fibromyalgia patients would not look to the same treatments as a neurologist, the doctor most chronic inflammatory patients would see. These are two different worlds of medicine and the neurologist pain doctor is unlikely to review fibromyalgia treatments for methods of treating chronic inflammatory pain. For example, the neurologist is likely to prescribe opioid analgesics, which will have the unintended consequence of actually lowering testosterone levels and exacerbating the pain.

The skilled practitioner in medical technology for the instant invention would not apply a testosterone gel therapeutic developed for non-inflammatory fibromyalgia tender point chronic pain to patients with inflammatory chronic pain. A clinician who treats inflammatory chronic pain patients would, at this time, be constrained on several levels from treating their patients using a therapeutic developed for fibromyalgia patients. First, prior to the instant invention, a mechanistic basis for the efficacy of a testosterone therapeutic for chronic inflammatory pain in humans had not been elucidated. Second, current paradigms of clinical practice, as well as reimbursement constraints, hold doctors to best practices that are limited to evidence-based mechanistic pathways that underlie pain. In fact, doctors are becoming ever more constrained to use evidence-based best-practice medicine. Thus, current medical practice, up to now, has failed to link concepts underlying reproductive immunology (White et al., "CD3+CD8+ CTL Activity Within the Human Female Reproductive Tract," J. Immunol., 1997, 158(6): 3017-3027), or therapeutics for fibromyalgia tender point pain (see U.S. Pat. Nos. 5,935,949 and 7,799,769), with androgen therapeutics for chronic inflammatory pain as described herein. Specifically, the "circle hypothesis" described herein has never been advanced prior to the instant invention. Third, off-label prescribing is limited by the FDA, which has stepped up its litigation against this, especially for therapeutics with abuse potential.

Identifying patients with chronic inflammatory pain states and clinical signs and symptoms of androgen deficiency. A) Reducing chronic inflammatory pain with androgen therapy. The instant invention relates to a method of reducing chronic inflammatory pain or state of distress in a human subject comprising diagnosing a human subject to have 1) any one of the following: a) elevated C-reactive protein, b) elevated erythrocyte sedimentation rate, c) any one of the following DSM-IV defined Disorders: Pain Disorder Associated With Psychological Factors 307.80, Pain Disorder Associated With Both Psychological Factors and a General Medical Condition 307.89, Dementia including Alzheimer's Type and Vascular Dementia 290, Alcohol-Related Disorders 291, Drug Withdrawal and Psychotic Disorders 292, Mood, Anxiety, and Mental Disorders 293, Dementia, Cognitive, and Amnestic Disorders including Head Trauma 294, Mood Disorder 206.90; Anxiety Disorders 300, Male and Female Sexual Disorders 302.70-302.74, 302.9; Alcohol and Drug Dependence Disorders 303, Alcohol, Drug, and Nicotine Abuse 305; Sleep Disorders 307.42; Acute Stress Disorder 308, Adjustment Disorders, including Post Traumatic Stress Disorder 309, Personality Disorders 310; Depressive Disorders 311; Sleep Disorders 327, Neuroleptic-Induced Disorders 332, 333; Male Sexual Disorders 607/608, Female Sexual Disorders 625; Age-Related Cognitive Decline 780.93, d) clinical symptoms of androgen deficiency, as described herein, or e) an unresolved state of distress as described elsewhere herein; and 2) determining if the subject has androgen levels in the lower half of the appropriate reference range. If the subject has at least one of the indications defined by (1) above, along with 2) androgen levels in the lower half of the appropriate reference range; a pain-reducing amount of a composition comprising an androgen can be administered to a human subject, wherein pain is reduced safely and effectively or the state of distress is ameliorated.

Identifying patients with chronic inflammatory pain states and clinical signs of androgen deficiency. B) Increasing a patient's pain threshold with androgen therapy. The instant invention also relates to a method of increasing the pain threshold of a human subject comprising diagnosing a human subject to have any one of the indications defined herein; determining if the subject has androgen levels in the lower half of the appropriate reference range; and, if the subject has at least one of the indications defined herein, along with androgen levels in the lower half of the appropriate reference range; administering a composition comprising a pain threshold-increasing amount of an androgen to a human subject, wherein the subject's pain-threshold is increased safely and effectively.

Testing and assessing patients for androgen therapy. The instant invention further relates to a method for determining if a human subject would benefit from androgen administration comprising any combination of the following tests and evaluations, as needed: A) testing for any one of the indications defined herein, B) testing the subject's serum to determine if their androgen levels are in the lower half of the appropriate reference range; C) assessing the subject for clinical symptoms of androgen deficiency which may include, but is not limited to, loss of libido, sexual dysfunction, chronic fatigue, anemia, low muscle:fat ratio, and alopecia, D) assessing levels of pain, E) assessing the subject's pain threshold, and/or F) testing using metrics that may include, but are not limited to, those for evaluating pain, physical function, psychological function, global health and sleep. If the subject meets the criteria for androgen treatment, a composition comprising an androgen can be administered to the subject, wherein the subject's androgen serum levels are restored to the middle-upper range of an appropriate reference range.

The invention also relates to a kit for determining if a human subject would benefit from androgen administration comprising instructions for diagnosing a subject as having an androgen-deficiency treatable by administration of an androgen. The instructions can comprise instructing a health care provider how to test the subject's androgen serum levels and how to determine if the subject meets any of the criteria described herein. The instructions can further comprise instructing the health care provider how to test the subject's pain threshold; and instructing the health care provider to administer a composition comprising an androgen to the subject if the subject has androgen levels in the lower half of the of the appropriate reference range, a low threshold of pain, and at least one of the indications described herein; so that the subject's androgen serum levels are restored to the middle-upper portion of an appropriate reference range, and clinical symptoms or the low pain threshold are improved safely and effectively.

The invention also relates to a method of increasing endogenous opioid peptide production in an androgen-deficient, endogenous opioid peptide-deficient human subject. The method comprises diagnosing a human subject to have at least one of a) elevated C-reactive protein, b) elevated erythrocyte sedimentation rate, c) DSM-IV disorder 307.80, d) DSM-IV disorder 307.89, or e) an unresolved stressor state; determining if the subject has androgen levels in the lower half of the appropriate reference range; determining if the subject low endogenous opioid peptide levels; and, if the subject has at least one of a) elevated C-reactive protein, b) elevated erythrocyte sedimentation rate, c) DSM-IV disorder 307.80, d) DSM-IV disorder 307.89, or e) an unresolved stressor state, along with androgen levels in the lower half of the appropriate reference range and low endogenous opioid peptide levels; administering a composition comprising an androgen to a human subject with androgen and opioid peptide deficiencies, wherein the subject's production of endogenous opioid peptides is increased.

In accordance with the present invention, androgen therapy is the primary therapy to be administered for all of the above embodiments of the invention. Further, in accordance with the invention, subjects receiving primary androgen therapy may also receive adjunctive opioid therapy if they have exogenous opioid-induced hypogonadism or other conditions that might require such adjunctive opioid therapy in addition to the primary androgen therapy. Further, while androgens remain the primary therapy for the methods of the instant invention, other compounds, such as, but not limited to, antidepressants may also be administered as adjunctive therapies.

BRIEF DESCRIPTION OF THE DRAWINGS

Certain aspects of the instant invention may be better understood by references to the detailed description when considered in connection with the accompanying Figures.

DETAILED DESCRIPTION OF THE INVENTION

Figure 1A:
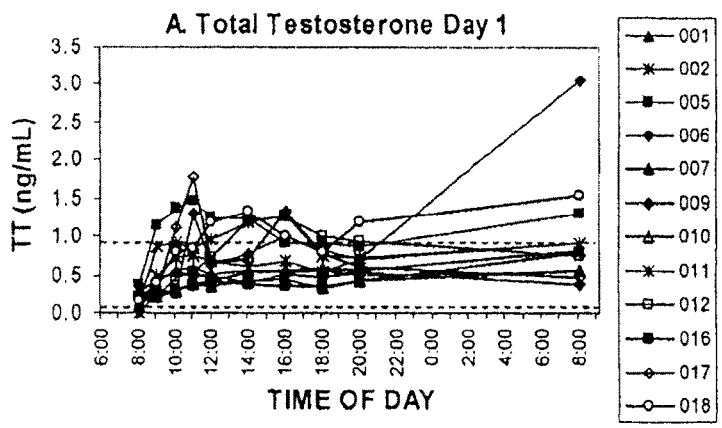
FIGS. 1A-1C show that the serum total testosterone concentrations in a population of female patients are increased in response to testosterone gel therapy.
Figure 1B:
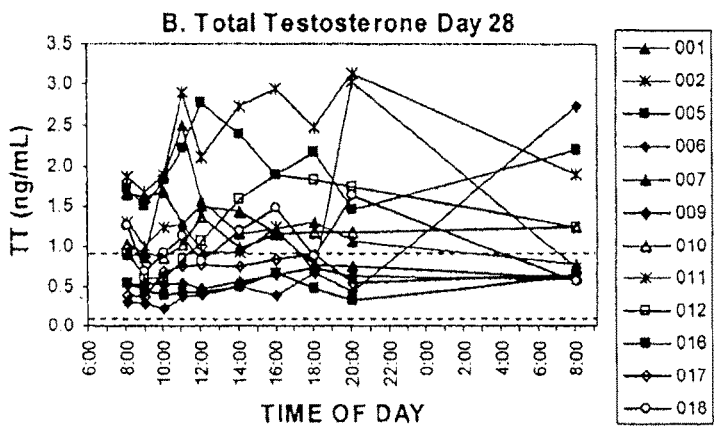
Figure 1C:
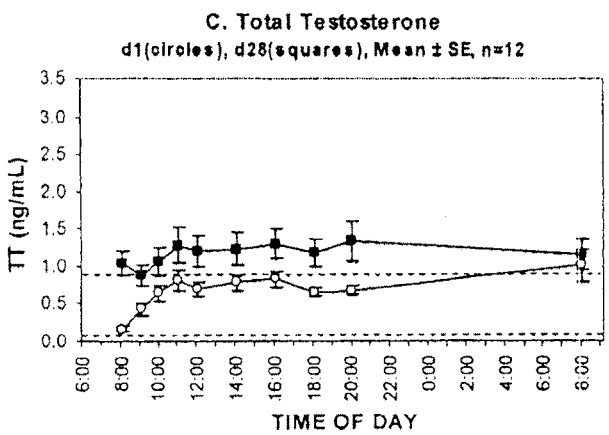
Figure 2A:
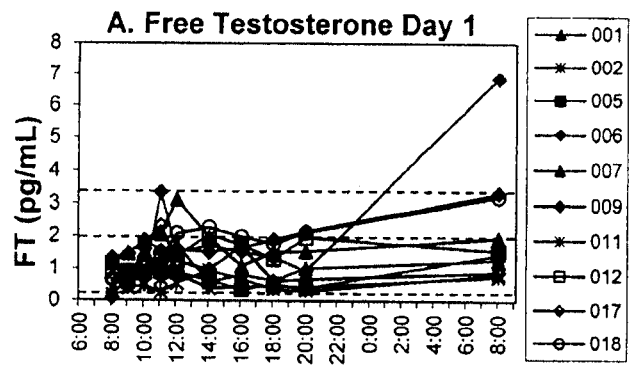
FIGS. 2A-2C show that the free testosterone concentrations in a population of female patients are increased in response to testosterone gel therapy.
Figure 2B:
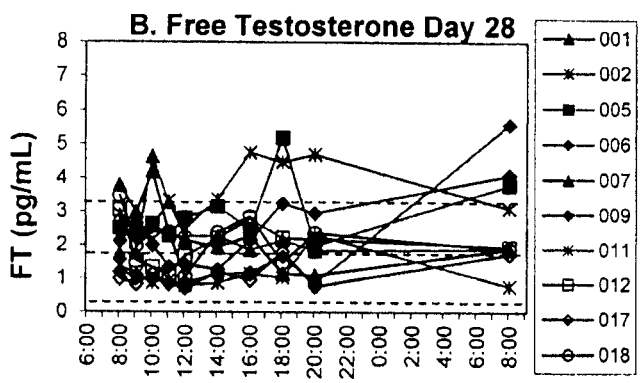
Figure 2C:
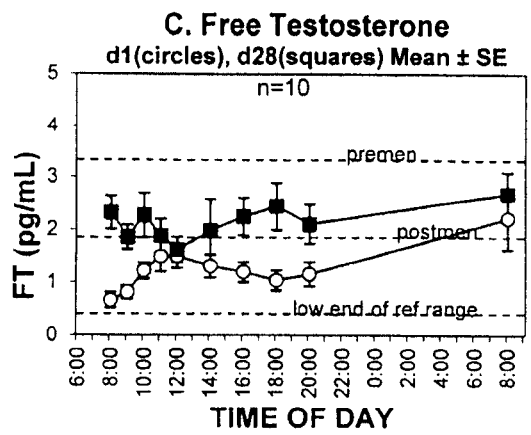

While the present disclosure may be embodied in many different forms, the drawings and discussions are presented with the understanding that the present disclosure is an exemplification of the principles of one or more inventions and is not intended to limit any one of the inventions to the embodiments illustrated.

Why androgen therapy is effective against unresolved pain, unresolved states of distress, or decreased tolerance to pain. The invention relates to how and why androgens are a critical part of pain pathophysiology, such that when androgens are given therapeutically to individuals with chronic inflammatory pain, the androgen treatment should significantly resolve that pain. By "androgen therapy" it is meant to include administration of a single androgen or a combination of androgens. Administration of the androgen can be a single administration or administration over a period of time. By "alleviate" it is meant to make less hard to bear, reduce or decrease, or lighten or relieve patients of the symptoms of an illness or a condition. By "androgen-deficient" or "androgen deficiency" it is meant that 1) a patient's testosterone serum levels are in the lower half of the reference range, and concomitant with at least one of the following: 2a) the presence of chronic or acute unresolved inflammatory pain (pain assessment as defined elsewhere herein) or state of distress or symptom of androgen deficiency, as described herein, 2b) the lack of a feeling of well-being combined with a low threshold of pain (threshold testing as defined elsewhere herein), or 2c) a failure to adapt to or resolve stress (stressors as defined elsewhere as a maladaptive and unresolved state of "distress"). By "primary therapy" it is meant to be the main or first-line therapy given to a subject for the treatment of chronic inflammatory pain, for increasing the pain-threshold of a subject, or for increasing a subject's production and/or levels of endogenous opioid peptides. By "adjunctive therapy" or "adjuvant therapy," it is meant to be a secondary therapy, given to a subject to augment or complement the subject's primary therapy.

Pain and stressor states are related and defined. Further, the focus of the present invention is on pain associated with stressors of various kinds, including, but not limited to: 1) PTSD, which includes combat or shell shock or Gulf War Syndrome, 2) accident, 3) trauma, 4) surgery, 5) autoimmune disease such as rheumatologic disorders, including arthritis, 6) chronic unresolved or acute viral infection, 7) infectious disease, 8) cancer, 9) chronic exhaustion or physical distress, 10) neuropathy, 11) hyperalgesia, 12) allodynia, 13) grief, emotional distress, or depression, 14) surgical or pharmacologic-induced gonadectomy, or 15) dysthymia. Also included are pain states with elevated levels of serum or cerebrospinal fluid Substance P, plus pain states with reduced levels of serum or cerebrospinal fluid endorphins and/or serotonin, dopamine, NMDA or enkephalinergics, all of which can cause chronic pain in females and in males. DSM-IV disorder coding for these conditions include code 307.80, "Pain Disorder Associated with Psychological Factors" (psychological factor plays a major role in pain); and code 307.89 "Pain Disorder Associated with Both Psychological Factors and a General Medical Condition" (psychological factors may or may not play a role in pain); including both acute and chronic pain; and including locations such as abdominal, back, bone, head or brain, legs, arms, internal organs, skin, immune system, nervous system and chest. Additional disorders that can affect pain are described herein. Stress, eustress and distress are defined herein. Further, a subject may have a chronic medical state accompanied by an additional stressor state, that causes or exacerbates chronic pain.

Figure 3A:
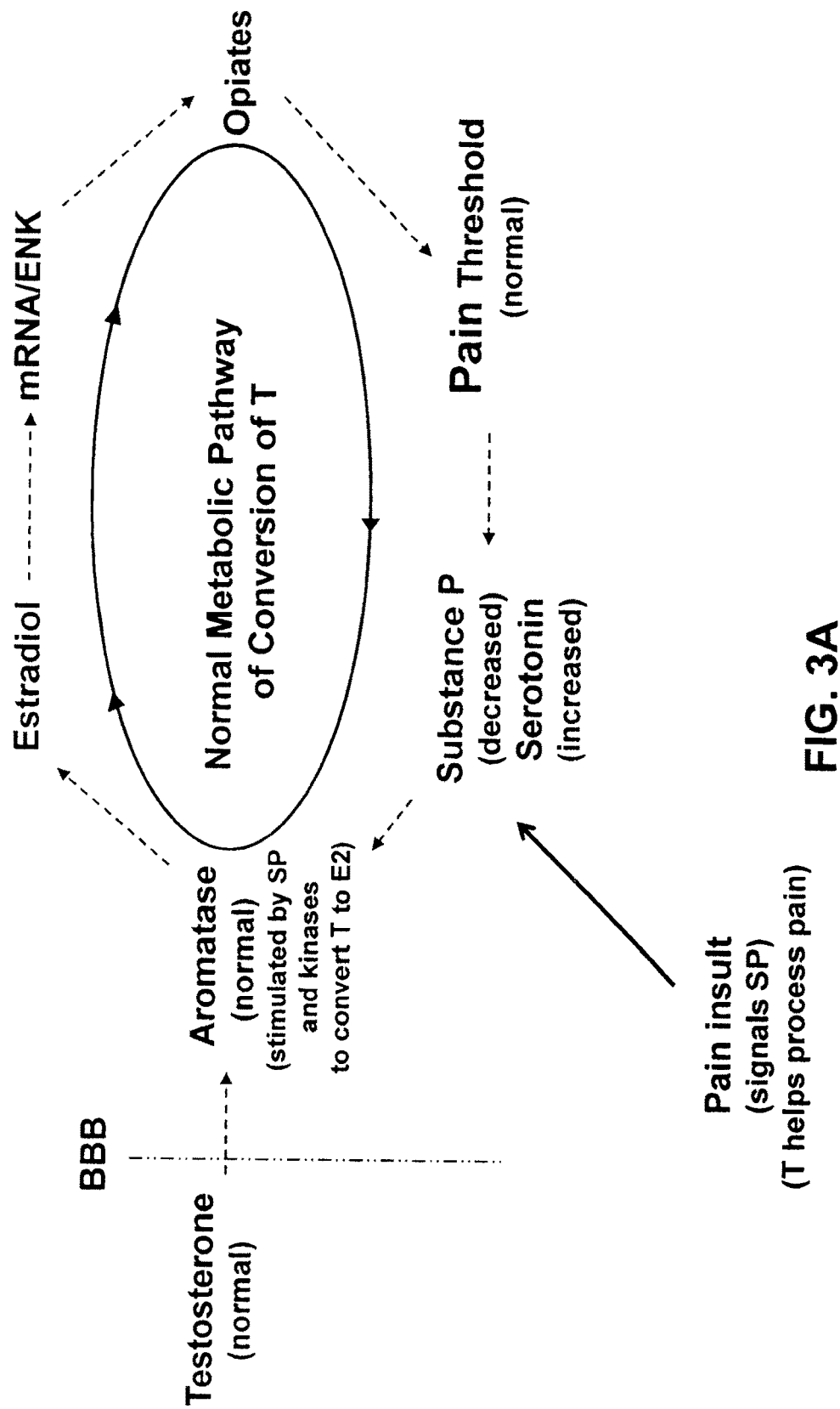
FIGS. 3A-3B depict the hypothesized metabolic pathway for testosterone in relation to nociception in the central nervous system in normal (A) and deficient (B) subjects.
Figure 3B:
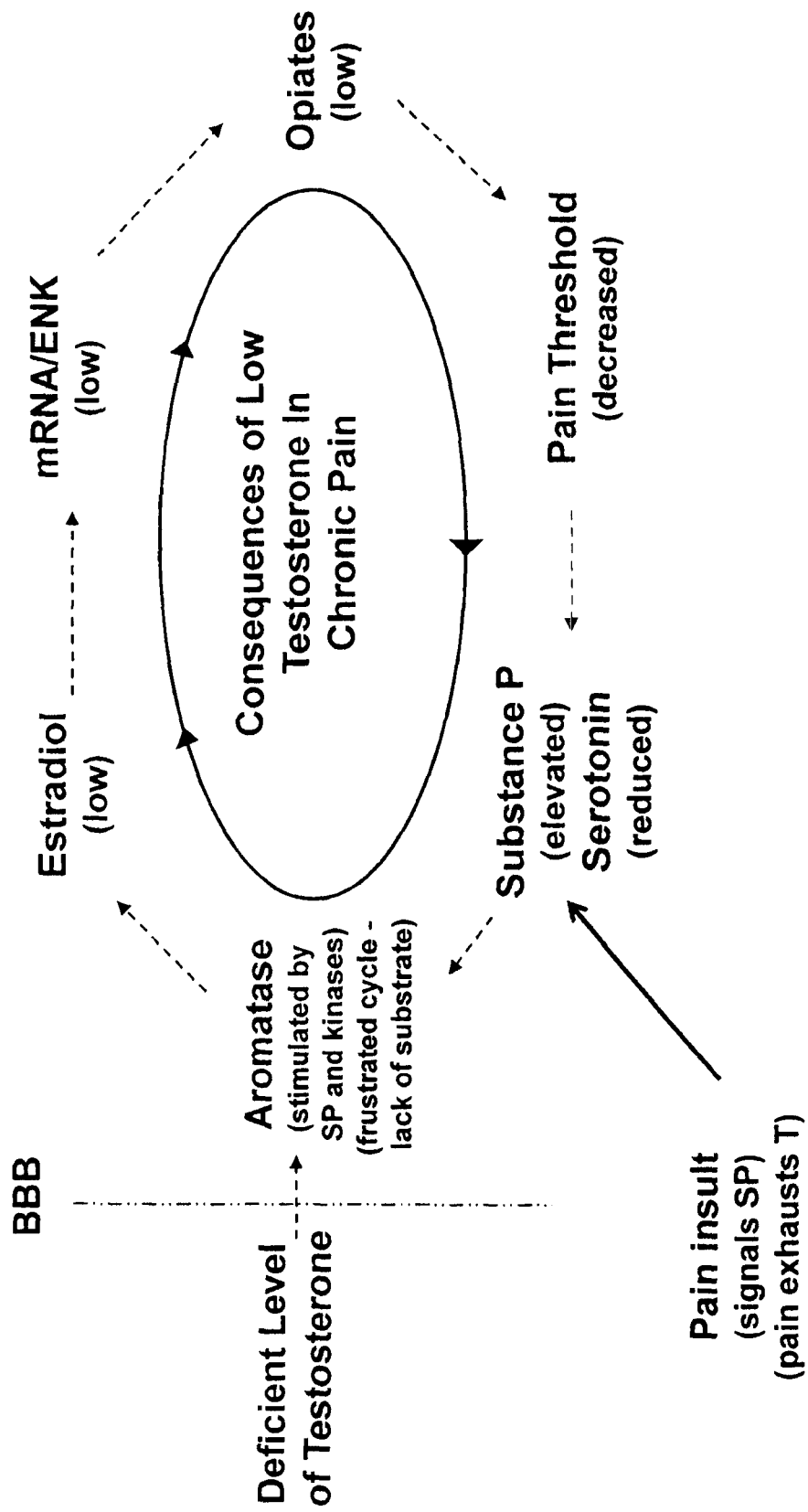

The fundamental basis or foundation of the instant invention (to treat chronic inflammatory pain with androgen therapy) is the combination of the following seemingly disparate observations in animals into a unifying pathway (the "Circle Hypothesis") that provides a mechanistic basis by which androgens dampen or down-modulate chronic pain in humans. FIGS. 3A-3B show the hypothesized metabolic pathway for testosterone in relation to nociception in the central nervous system. FIG. 3A depicts the pathway in normal individuals. Overview of Circle Hypothesis in the healthy state: A painful stimulus, state of stress, or trauma is signaled by an increase in Substance P. Pain, stress or trauma also causes serotonin levels (and other stress-mediating neurochemicals that help regulate the descending control of pain (M. J. Millan, Progress in Neurobiology, 2002 66:355-474) to drop or be altered. This results in a loss of feeling of well-being. Substance P has been found to stimulate the enzyme aromatase within the central nervous system nociceptive relay neurons in a highly regulated process that is mediated by protein kinases and phosphoprotein phosphatases, which phosphorylate and de-phosphorylate aromatase (respectively), consistent with their status as classic "gate-keeper" regulators of cell function. Aromatase is thereby stimulated to act upon its substrate testosterone, which can be provided from the periphery and can cross the blood-brain barrier (BBB) for this purpose (also a highly regulated process, see elsewhere herein), to convert it to 17-beta estradiol within the dorsal horn of the spinal cord in the CNS. Increases in 17-beta estradiol cause the subsequent upregulation of mRNA encoding enkephalins (opioid peptides) in the spinal cord dorsal horn nociceptive relay neurons. These opioid peptides can both down-regulate Substance P (Zachariou et al., Euro. J. Pharmacol., 1997, 323:159-165), as well as dampen pain and bring stressor states toward healthy baseline states (eustress). The decrease in Substance P, along with concomitant increase in serotonin levels, also helps dampen or "wind-down" pain and return to the pre-painful/stressful state or "homeostasis," i.e., a feeling of well-being.

Aromatase is not only found in the nociceptive relay neurons in the spinal cord, but also in the brain and the periphery, where it can be a critically important player with respect to pain pathways at any of these sites. In addition, there are mechanisms that favor entry of testosterone (over estrogen) from the periphery through the blood-brain barrier into the central nervous system. These mechanisms involve, in part, sex hormone binding globulin (SHBG) and the complex regulation of aromatase and its substrate testosterone.

Overview of Circle Hypothesis in the androgen deficient or unhealthy state: FIG. 3B shows the same cycle in patients having chronic pain, which may be related to any of the stressors as defined herein. Chronic inflammatory pain states or unresolvable stress or trauma can lead to a dys-equilibrium, or state of distress, which is not appropriately resolved in these patients. Thus, patients with inadequate or too-low androgen/testosterone are predicted to have a "frustrated cycle" as follows: The pain processing pathways above, pathways that normally resolve pain and return the patient to a healthy state (eustress), now unremittingly utilize testosterone that has transited across the BBB into the CNS from the periphery, ultimately resulting in testosterone exhaustion within the spinal cord dorsal horn nociceptive relay neuron. As above, Substance P, acting as a signal for pain or stress, stimulates aromatase within the dorsal horn. However, because testosterone has been exhausted and depleted, the aromatase enzyme has no available substrate, and thus, aromatase is involved in a "frustrated cycle," being unable to convert testosterone to 17-beta estradiol. Further, because testosterone has been depleted and 17-beta estradiol is not expressed, opioid peptides (enkephalins) are not up-regulated, and the opiate-mediated dampening of nociceptive signals fails to occur, resulting in abnormal, chronic, ever-widening and diffuse pain "wind-up" phenomena. The frustrated cycle results in the repetitive action of nociceptive C-fibers, augmented pain, and hyperalgesia, i.e., hypersensitivity to pain and a decreased threshold to pain. Substance P remains elevated, serotonin remains reduced, and a patient will remain in a hypersensitive pain state, or at high risk of pain with an abnormally low threshold for pain, with a lack of feeling of well-being, until the pain processing cycle is restored, for example, via androgen or testosterone replacement therapy. In summary, chronic pain can exhaust testosterone, the cycle is frustrated, and pain is not appropriately processed. The insufficient testosterone levels fail to mediate recovery from a painful stimulus, inflammatory pain, a stressor, or a state of trauma, resulting in a new dys-equilibrium or state of distress, that, in time, sets up altered neuronal circuitry or patterns through a process called neuronal plasticity, thereby allowing the distressed state to become entrenched.

Essentially, this is consistent with a mechanism by which enkephalins, endorphins, and other opioid peptide molecules stimulate inhibitory receptors on nociceptive relay neurons. In turn, release of excitatory effectors, such as Substance P, is inhibited, with the inhibitory receptors in a location next to where the excitatory effectors are released (Zachariou et al., Euro. J. Pharmacol., 1997, 323:159-165). While others have contributed knowledge toward these concepts, particularly in animals, testosterone therapy has not yet been used for all the diverse types of chronic inflammatory pain seen in the clinic, pain which may be resistant to current common and standard pain therapeutics.

Details of the Circle Hypothesis. It is known that Substance P, acting as neurotransmitter, can transmit painful impulses along the ascending pain pathways within the CNS. (Foldes, 1991 Anaesthesiol. Reanimat., 2005, 16:287-298; Siemion et al., Amino Acids, 2005, 29:161-176). Substance P is also a marker of inflammation. Thus, Substance P allows communication between the immune and neuroendocrine systems, and within the nervous system between the periphery and CNS, to mediate nociceptive signaling. It is known that the sex steroid hormones can induce opioid peptides within the spinal cord dorsal horn, and further, that opioid peptides can inhibit Substance P (Zachariou et al., Eur. J. Pharmacol., 1997, 323:159-165). This invention relates to underlying causes of chronic pain states, and likely relates to individuals who experience a stressful event either 1) at a time when their sex steroid hormone concentrations are too low to properly attenuate pain signals, or 2) the stressor itself has exhausted the testosterone, either of which results in a failure to appropriately down-modulate nociceptive relay signals and dampen wind-up pain phenomena. Both of our patient types, patients with chronic unresolvable inflammatory pain, and distressed patients with abnormally low pain thresholds, can be understood in the context of this "Circle Hypothesis."

Substance P (P stands for "powder," as it was discovered in a dried acetone powder of a neural tissue extract) is one of several neurokinin peptides, which are also known as tachykinin neuropeptides. These peptides are generally from about ten to about 12 amino acids in length, and function to excite neurons, evoke behavioral responses, and to contract smooth muscles. In addition, these peptides are potent vasodilators. In humans, neurokinins are encoded by two tachykinin genes TAC1 and TAC3. TAC1 encodes neurokinin A (previously known as Substance K), neuropeptide K (also known as neurokinin K), neuropeptide gamma and Substance P. The different splice forms of the TAC1 gene result in the production of the different neurokinins. The TAC3 gene encodes neurokinin B. As described above, Substance P is involved in nociception, transmitting painful inflammatory insults and information about tissue damage from peripheral receptors to the CNS, and as such, it is a well-known marker for inflammation. It functions as both a neurotransmitter and a neuromodulator.

The thymus may also play a role in chronic inflammatory pain. The thymus is known as a "primary lymphatic organ" responsible for maturing and developing or "educating" thymic cells so they can emigrate to peripheral tissues and respond to "danger," distress, pathogens, etc., that assail the host. Thymic T cells are a major component and driving force in inflammatory responses, responding to the dangers that are perceived by the immune system. These lymphocytes are tightly regulated in a bi-phasic way such that they initially proliferate (expansion phase) in response to disease such as infection. Once the insult is cleared and the immune system no longer perceives danger, those responding T cells go through a contraction phase and are down-regulated or programmed to die in order to re-establish a quiescent level ("eustress"). Chronic inflammatory pain states involve an out-of-balance and undampened expansion of immune cells, an environment of inflammation that can be autoimmune-like, and a failure to return to a quiescent non-inflammatory state, resulting in pain, soreness and inflammation that is not appropriately resolved ("distress"). Common markers associated with chronic inflammatory pain states include, but are not limited to, Substance P, elevated erythrocyte sedimentation rate, and elevated C-reactive protein or CRP. Gonadal steroid hormones can act to dampen inflammatory cells, and concomitant with this, the conversion of testosterone to estrogen by aromatase within the CNS dampens nociception in the dorsal horn nociceptive relay neuron. This pain signaling down-modulation likely occurs within the CNS descending pathways of nociceptive relay neurons to resolve pain. For a general review of descending neural pathways from cerebral structures to the dorsal horn of the spinal cord that control pain (see Millan, M. J. "Descending control of pain", Progress in Neurobiology, 2002, 66:355-474). The instant invention involves raising serum levels of testosterone to higher levels, levels that are safe within the reference range and clinically effective, and that can down-modulate inflammatory pain signaling and alleviate fatigue such that a healthy quiescent state (eustress) is promoted with feelings of well-being.

Sources of endogenous androgens and the role of the HPA/HPO axis in distress. The chronic stress that induces adrenal hyporesponsiveness may also further decrease androgen production by the adrenal gland. The adrenal gland accounts for approximately 25% of circulating testosterone concentrations in normal individuals, with an additional 25% from the gonads (post-menopausal ovaries normally continue to produce some androgens) and 50% from pre-hormones, primarily androstenedione, derived from both the adrenal gland and gonads. Sex steroid hormone production has been found to be exhausted and/or down-modulated in response to stress (Opstad, J. Clin. Endocrin. Metab., 1992 74(5):1176-1183) via the HPA (hypothalamus-pituitary-adrenal) axis in addition to the HPO (hypothalamus-pituitary-ovary/gonad) axis. Thus, adrenal hyporesponsiveness due to chronic stress could result in significant decreases in testosterone production and could add to diminished gonadal function.

Chronic pain experienced by patients is thought to be related to a dysfunctional stress response within the HPA axis, i.e., an exaggerated ACTH response and decreased cortisol response indicating adrenal hyporesponsiveness to the master stress hormone CRH (corticotropin releasing hormone), that persists after the initiating event has been resolved. Significantly elevated Substance P concentrations can be found in the cerebrospinal fluid of all types of chronic inflammatory pain patients, which likely relates to increased pain signaling in these patients since, in the periphery, Substance P can induce mast cell degranulation and release of histamine which can directly excite nociceptive neurons (along with inflammatory immune cells) and amplify wind-up phenomena in chronic pain states.

A role for the sex steroid hormones in nociceptive pain processing. Data support a role for androgens and estrogens in opiate production in the nociceptive relay cells that transmit pain signals in the dorsal horn of the spinal cord, providing a mechanistic basis for testosterone involvement in pain perception. This basis is likely related to "gate control theory," in which negative modulatory neurologic signals down-modulate nociceptive pain signals and restore the resting healthy state or homeostasis (the state of "eustress"). The loss of homeostasis due to stressors (the state of "distress") in chronic pain patients is likely exacerbated and driven by stress-induced exhaustion or catabolism of testosterone to the point of a testosterone deficient state. Neuronal plasticity, the ability of neuroendocrine pathways to enter into an altered set of equilibria that can be associated with pathology, called "allostasis" or "allostatic load," according to Melzack (Pain Mechanism: A New Theory, Science, 1965, 150(3699):971-979) and others (or a state of "distress," according to Selye), then allows for hypersensitivity to pain, amplification of pain, pain field widening (wind-up phenomena), such that a chronic pain state can become entrenched. The immune system, as well as neuronal-derived immunologic mediators of pain, frequently contribute to this pathology as well.

Combining the concept of stressors and stressor states and pain, with the concept of androgen therapy to treat chronic inflammatory pain, is a novel and unique idea. Chronic inflammatory pain has many different clinical manifestations and known causes. However, the importance of stressor states has not been well understood, and has not been addressed, in the etiology of chronic inflammatory pain conditions. In addition, the consideration of a healthy sex steroid hormonal balance is not standard practice within the pain clinic arena. A stressor state, whether acute or long-standing, takes a toll on a patient's systemic defenses and compromises the hormonal balance, thereby influencing the patient's painful condition.

Patients entering a stressor state, as described below, are at high risk for chronic pain from two sources. First, if a subject manifests low testosterone, is borderline testosterone-deficient, or becomes testosterone-deficient, and if such a subject then enters a stressor state, chronic pain can more readily occur. Thus, the subject is at higher risk and has greater susceptibility to pain states and clinical "distress" states. Second, if a subject with a painful condition, despite normal androgen levels initially, enters a stressor state, such subject's acute pain can become chronic pain due to androgen exhaustion and the development of an androgen-deficiency state. In both cases, androgen deficiency, and symptoms thereof, result in the failure of opiates to be produced that would otherwise dampen nociceptive pain relay cells in the dorsal horn of the spinal cord and promote feelings of well-being.

Evidence for the ability of stressors to cause androgen exhaustion can be found in military personnel undergoing rigorous training. Opstad, (J. Clin. Endocrin. Metab., 1992, 74(5):1176-1183) discloses that personnel taking part in 5-day military endurance training courses that require physical activities on a round-the-clock basis show a decrease in the plasma levels of several androgenic compounds, including testosterone, dehydroepiandrosterone, androstenedione, as well as 17α-hydroxyprogesterone. Plasma levels of these compounds can decrease under stress conditions by as much as 60% to 80%.

Preclinical animal studies are consistent with the concept that androgens can be important for dampening pain signaling via nociceptive relay neurons in the spinal cord, but are not predictive of studies in humans with chronic pain, unlike the present invention. Testosterone is known to be important within the central nervous system in preclinical studies, although this has not translated into the clinic. Androgen receptors can be widely found in specific patterns of expression throughout the CNS in various animal models. And testosterone concentrations have been shown to be dramatically decreased in the brain and spinal cord of rats in response to pain-inducing subcutaneous injections of formalin into the paw. In these animals, the loss of testosterone in the central nervous system was demonstrated to be due to its metabolism by 5α-reductase to dihydrotestosterone (Amini, H. et al., Pharmacol. Biochem. Behav., 2002, 74:199-204). These authors pointed out that dihydrotestosterone can be metabolized to 5α-androstane-3α,17β-diol, which is an effective modulator of $GABA_A$ receptor complexes in the brain. $GABA_A$ receptors are found throughout the brain, and actions of $GABA_A$ receptor modulators in the limbic system, specifically in the amygdala, are associated with feelings of fear. The $GABA_A$ receptor ion channel complex is an inhibitory ion channel in the brain. Thus, testosterone may be relevant not only for modulation of pain but also for feelings of emotional well-being via binding of its metabolites to the neurosteroid site of the $GABA_A$ receptor, although this remains to be verified.

A cause-and-effect relationship between testosterone and pain sensation has been suggested in animal models. For example, evidence supports the concept that sex hormones can elevate the pain threshold in rodents, for example, during pregnancy (Gintzler, A. R., Science, 1980, 210:193-195), when testosterone concentrations, as well as estrogen and progesterone concentrations, are elevated both in animal models and humans (Bammann, B. L. et al., Am. J. Obstet. Gynecol., 1980 137:293-298). However, the usage of androgens in humans to either dampen chronic inflammatory pain or elevate an individual's pain threshold has not been considered or tested.

In other animal studies, aromatase-positive cells have been found in the spinal cord dorsal horn of higher vertebrates (quail), where initial processing of pain sensation occurs (Blomqvist, A., Compar. Neurol., 2000 423:549-551; Evrard, H. et al., J. Comparative Neurology, 2000, 423:552-564). The presence of aromatase, which converts testosterone to 17β-estradiol, is interesting because it is known that estrogen can induce the transcription of opiates in estrogen receptor-positive cells derived from the superficial layers of the spinal dorsal horn (Amandusson, A. et al., Neurosci. Lett., 1996 196:25-28; Amandusson, A. et al., Eur. J. Neurosci., 1996, 8:2440-2445; Amandusson, A. et al., Pain, 1999 83:243-248), a location in the nociceptive pain relay neurons that is important for the synthesis of endogenous opiates. Administration of estrogen to ovariectomized female rats has been demonstrated to increase spinal cord enkephalin transcription (Amandusson, A. et al., Pain, 1999, 83:243-248), and estrogen receptor-positive cells co-localize with preproenkephalin mRNA (Amandusson, A. et al., Eur. J. Neurosci., 1996, 8:2440-2445). These endogenous opiates act on enkephalinergic neurons to mediate inhibition of nociceptive relay cells, both in primary afferent fibers as well as in pain-modulating fibers descending from the brainstem (Ma, W. et al., Neuroscience, 1997, 77:793-811). While there is good reason to think it is testosterone, rather than estrogen, that is more important for dampening pain, due in part to differential regulation by SHBG (sex hormone binding globulin) of the ability of estrogen vs. androgens to cross the blood-brain barrier, an animal dosed with sufficient estrogen may still have a reduction in pain. However, estrogen or estrogen-progestin hormone replacement therapy (HRT) in women is not known to be particularly effective with respect to being anti-nociceptive. Thus, androgens, rather than estrogens, appear to be the relevant hormone for effective migration from the periphery into the CNS to dampen pain.

Further evidence for the importance of androgens in dampening pain is found in studies where gonadectomy of male and female rats has resulted in increased pain responses (i.e., a lower pain threshold) to the formalin test (with verified decreased testosterone and increased estradiol plasma levels in male rats). Conversely, treatment with testosterone has resulted in decreased pain responses concomitant with increased testosterone plasma levels. Furthermore, exposure of female mice to testosterone just after birth induces pharmacologically defined patterns of analgesia in adults that are similar to male pathways. In at least two studies, however, male or female gonadectomy resulted in improved analgesia in rats (Nayebi and Ahmadiani, Pharmacol. Biochem. Behav., 1999, 64:467-71; Stoffel et al., J.

Pain, 2005, 6(4):261-274). The fact that these in vivo animal study results are disparate shows that the preclinical experiments and animal models discussed above, while suggestive, are not predictive of efficacy or safety in human subjects. Therefore, it is desirable to be able to directly assess the ability of androgen therapy to dampen pain in humans. Further, it is desirable to be able to use androgen therapy in the treatment of chronic pain conditions. Confounders of age, and additional facets of sexual dimorphism relating to gender differences between males and females in development and otherwise in relation to pain processing point to the unpredictable nature of chronic pain treatment in humans. In summary, while preclinical animal model experiments suggest the concept that testosterone, or other androgens, may down-modulate pain in adult males and females, the inventor has unexpectedly found that androgens can be used to successfully treat chronic pain in humans.

Chronic opioid usage can lower testosterone levels due to suppression of the HPG (Hypothalamic Pituitary Gonadal) Axis. Preclinical animal studies that demonstrate an effect on nociception in gonadectomized rats (despite mixed and complex findings), have led clinical pain specialists to look at the apparent side effects of androgen deficiency symptoms associated with long term opioid usage in their chronic pain patients. So, for these patients, not only is chronic opioid usage known to exacerbate or worsen pain sensitivity (demonstrating the complexity of opioids and their relationship to pain), but chronic opioid therapy-associated androgen-like deficiency symptoms is thought to occur via opioid down-regulation of the HPG axis, primarily through the suppression of gonadotropin-releasing hormone (GnRH), which can result in decreased production of the sex steroid hormones, including testosterone (for example, Abs et al., J. of Clin. Endocrinol. Metab., 2002, 85(6):2215-2222). The ability to assign cause and effect with respect to the interplay between sex steroid hormones and nociception, and the ability to provide a comprehensive and logical mechanism, however, remains elusive.

Along these lines, it is relevant to uncover the flawed assumptions under which clinicians, who contemplate testosterone replacement therapy in patients on maintenance opioid treatment, view the role of testosterone. Tennant et al. discloses four chronic pain subjects already on maintenance opioids as primary therapy for chronic pain, who were given adjunctive testosterone therapy to try to improve the well-being of these patients ("Testosterone Replacement in Chronic Pain Patients," Practical Pain Management, 2010, 12-15). In each of these subjects, testosterone (always as the adjunctive therapy in combination with primary opioid therapy) anecdotally and purportedly, resulted in an improved quality of life. However, it is difficult to draw any conclusions from the study since 1) the study consisted of only four patients, 2) there were no uniform inclusion/exclusion criteria, 3) there was no control group, 4) no statistical analysis was performed, 5) statistical significance was not demonstrated, 6) testosterone was not tested as a primary therapy by itself, i.e., without opioids, 7) the end point studied was only changes in quality of life, 8) pain was not tested as an end point, and 9) the additional drugs and/or hormones administered to the patients in combination with the opioid-testosterone combination therapy confounded any results that might have been seen.

Tennant advances an entirely different mechanism from the instant application. Even if Tennant's anecdotal reports could be considered meaningful, Tennant never suggested or considered that testosterone, by itself or as a primary therapy, was a treatment for pain, that testosterone might have a direct effect on pain, or that testosterone might have analgesic properties by itself. As for a possible mechanism, Tennant hypothesized that any analgesic effect would be from the exogenous opioids. Since Tennant never considered that testosterone can act directly on nociception, he never tested testosterone alone as a primary therapy with or without opioid treatment. Tennant believed that testosterone aided the activity of the primary therapy opioids by improving the binding of opioid peptides to their opioid receptors. In Tennant's mind, a study of testosterone alone would make no sense since testosterone could have an effect only in combination treatment with the primary therapy exogenous opioids to augment their pharmacologic effect.

Daniell cited the same studies as those cited by Tennant and concluded similarly that anti-nociception would be mediated by exogenous opioids, not testosterone, and that testosterone replacement therapy was acting to alleviate non-pain symptoms in patients on maintenance opioid therapy. Daniell et al. carried out an open-label study (without placebo) in males on maintenance or primary opioid therapy to determine if adjunctive testosterone therapy could reverse the non-pain symptoms of testosterone deficiency, including sexual function, mood and depression (Daniell et al., "Open-label pilot study of testosterone patch therapy in men with opioid-induced androgen deficiency," J. Pain, 2006, 7(3):200-210). Pain was assessed to determine if the action of the opioids as primary therapy could be improved, but no significant change was found in the pain severity score. Daniell concluded that "It is difficult to interpret these findings in the absence of a placebo group."

How the instant invention differs from Tennant and from Daniell. The basis for both Tennant's and Daniell's reasoning, including an explanation of the flaws in their reasoning, is as follows: 1) Stoffel et al. carried out a study in rats in which gonadectomy sometimes decreased, and sex steroid hormones sometimes increased, opioid receptor agonist-induced anti-nociception (Stoffel et al., J. Pain, 2005, 6(4): 261-274). However, Stoffel actually concluded that because the effects were so variable, sex hormone influence on opioid analgesia was not likely to be an effect of sex hormones on nociception, but instead "might be more readily explained by organizational effects of gonadal steroids" on opioid receptors. This type of variable data, both in male and female animals, in which gonadectomy can increase (rather than decrease) pain thresholds, has also been confirmed by others (see, e.g., Nayebi and Ahmandiani, Pharmacol. Biochem. Behav., 1999, 64:467-471). 2) Tennant incorrectly cites a study by Holaday et al. as evidence for a relationship between testosterone and opioids (J. Pharmacol. Exp. Therapeut., 1979, 208(2):176-183). The Holaday study does support an interplay between glucocorticoids and opioids, but there is no mention or contemplation of an interplay between the sex steroid hormones and opioids. 3) Tennant incorrectly cites a study by Long and Holaday as evidence that testosterone improves transport of opioids across the blood-brain barrier (Science, 1985, 227:1580-1583). In reality, Long and Holaday provide evidence that adrenal-cortex function (via adrenalectomy vs. adrenal demedullation, and corticosterone (glucocorticoid) replacement) modulates the permeability of brain tissue to isotopically labeled BSA. Sex steroid hormones, quite different functionally from glucocorticoids (although both are produced in the adrenal cortex), are not mentioned or contemplated in the Long and Holaday study. Unlike the instant invention, Tennant and Daniell both fail to consider the possibility that the relevant mechanism with respect to the blood-brain barrier and its relationship with nociception might be the regulation by sex hormone binding globulin (SHBG) of testosterone transiting across the BBB, for usage as the substrate for aromatase within the dorsal horn of the nociceptive relay neuron (for which there is evidence, see, e.g., MacLusky et al., Science, 1981, 211:1294-1303). 4) Both Tennant and Daniell assess androgen replacement therapy as an adjunctive therapy in chronic pain patients on primary therapy maintenance opioids by looking for improvement of testosterone deficiency symptoms, and the symptoms listed do not include pain, other than that mediated by the primary opioid therapeutics, an indication that neither Tennant nor Daniell consider testosterone's mechanism of action to be pain related. Rather, testosterone is evaluated as an adjunctive therapy both by Tennant (see Table 3) and Daniell for improving non-pain quality of life symptoms In conclusion, it has been recognized for some time that various drugs and treatments, including opioids and antidepressants, can have the side effect of decreasing testosterone levels. Unlike the instant invention, however, those of skill have never considered taking this concept further to the next step, that treating a chronic pain patient with testosterone as a primary therapy or alone, without opioids, can safely, statistically and significantly improve pain symptoms via testosterone's ability to upregulate endogenous opioid peptides within the nociceptive neurons in the spinal cord (Circle Hypothesis)—without the morbidities and side effects of primary therapy with exogenous opioids. Nor has anyone provided a comprehensive and logical mechanism by which this happens, unlike the instant invention, which provides detailed, strong evidence for the biologic pathways underlying testosterone's ability to act directly, in the absence of exogenous opiates, as an anti-nociceptive pain therapeutic in humans.

The invention relates to a method of reducing inflammatory pain or ameliorating a clinical state of "distress" in a patient with symptoms of androgen deficiency and/or with an abnormally low pain threshold (and consequently a high susceptibility or risk of having a chronic inflammatory pain state): Overview. The invention relates to a method of reducing inflammatory pain or a clinical state of distress, as described herein for example, in an androgen-deficient human subject comprising diagnosing a human subject to have at least one of the indications defined herein; determining if the subject has serum androgen levels in the lower half of the appropriate reference range; and if the subject has at least one of one of the indications defined herein, along with androgen levels in the lower half of the appropriate reference range; administering, as primary therapy, a composition comprising a pain-reducing amount of an androgen to human subject having symptoms of androgen deficiency, wherein pain is reduced safely and effectively. The invention also contemplates the administration of a composition consisting essentially of a pain-reducing amount of an androgen to a human subject having symptoms of androgen deficiency, wherein pain is reduced safely and effectively.

For each of the following embodiments of the invention the term "elevated" means at the high end or above the normal or reference range of values for the measured statistic, the measured statistic including, but not limited to, C-reactive protein, erythrocyte sedimentation rate, or Substance P levels. The term "decreased" means below or at the low end of the normal or reference range of values for the measured statistic, the measured statistic including, but not limited to, the levels of endogenous opioid peptides.

The invention relates to methods of reducing chronic inflammatory pain in a human subject. Specifically, the invention relates to a method of reducing chronic inflammatory pain in a human subject with androgen deficiency symptoms comprising diagnosing a human subject to have at least one of a) elevated C-reactive protein, b) elevated erythrocyte sedimentation rate, c) DSM-IV disorder 307.80, d) DSM-IV disorder 307.89, or e) an unresolved stressor state; determining if the subject has androgen levels in the lower half of the appropriate reference range. If the subject has at least one of a) elevated C-reactive protein, b) elevated erythrocyte sedimentation rate, c) DSM-IV disorder 307.80, d) DSM-IV disorder 307.89, or e) an unresolved stressor state, along with androgen levels in the lower half of the appropriate reference range; the method includes administering a composition comprising a pain-reducing amount of an androgen to the human subject with androgen deficiency symptoms, wherein pain is reduced safely and effectively. This embodiment of the invention also contemplates the administration of a composition consisting essentially of a pain-reducing amount of an androgen to a human subject having symptoms of androgen deficiency, wherein the subject's pain is reduced safely and effectively.

Alternatively, the invention relates to a method of reducing chronic inflammatory pain in a human subject with androgen deficiency symptoms consisting essentially of diagnosing a human subject to have at least one of a) elevated C-reactive protein, b) elevated erythrocyte sedimentation rate, c) DSM-IV disorder 307.80, d) DSM-IV disorder 307.89, or e) an unresolved stressor state; determining if the subject has androgen levels in the lower half of the appropriate reference range. If the subject has at least one of a) elevated C-reactive protein, b) elevated erythrocyte sedimentation rate, c) DSM-IV disorder 307.80, d) DSM-IV disorder 307.89, or e) an unresolved stressor state, along with androgen levels in the lower half of the appropriate reference range; the method includes administering a composition comprising a pain-reducing amount of an androgen to the human subject with androgen deficiency symptoms, wherein pain is reduced safely and effectively. This embodiment of the invention also contemplates the administration of a composition consisting essentially of a pain-reducing amount of an androgen to a human subject having symptoms of androgen deficiency, wherein the subject's pain is reduced safely and effectively.

The invention relates to methods of increasing the pain threshold in a human subject. The invention also relates to a method of increasing the pain threshold of an androgen-deficient human subject comprising diagnosing a human subject to have at least one of the indications defined herein; determining if the subject has androgen levels in the lower half of the appropriate reference range; and, if the subject has at least one of the indications defined herein such as having an unresolvable state of distress, along with androgen levels in the lower half of the appropriate reference range; administering a composition comprising an androgen as primary therapy to human subject having symptoms of androgen deficiency, wherein the subject's pain-threshold is increased safely and effectively. This embodiment of the invention also contemplates the administration of a composition consisting essentially of a pain threshold increasing amount of an androgen to a human subject having symptoms of androgen deficiency, wherein the subject's pain threshold is increased safely and effectively Alternatively, the invention relates to a method of increasing the pain threshold of an androgen-deficient human subject consisting essentially of diagnosing a human subject to have at least one of a) elevated C-reactive protein, b) elevated erythrocyte sedimentation rate, c) DSM-IV disorder 307.80, d) DSM-IV disorder 307.89, or e) an unresolved stressor state; determining if the subject has androgen levels in the lower half of the appropriate reference range. If the subject has at least one of a) elevated C-reactive protein, b) elevated erythrocyte sedimentation rate, c) DSM-IV disorder 307.80, d) DSM-IV disorder 307.89, or e) an unresolved stressor state, along with androgen levels in the lower half of the appropriate reference range, the method includes administering a composition comprising a pain-threshold increasing amount of an androgen to a human subject with androgen deficiency, wherein the subject's pain threshold is increased safely and effectively. This embodiment of the invention also contemplates the administration of a composition consisting essentially of a pain threshold increasing amount of an androgen to a human subject having symptoms of androgen deficiency, wherein the subject's pain threshold is increased safely and effectively The invention relates to method of testing if a human subject would benefit from androgen administration. The invention further relates to a method for determining if a human subject would benefit from androgen administration comprising testing for at least one of the indications defined herein; determining if the subject has androgen levels in the lower half of the appropriate reference range; testing the subject's pain threshold; and if the subject has at least one of the indications defined herein, along with androgen levels in the lower half of the appropriate reference range and a low threshold of pain, administering a composition comprising an androgen to the subject as the primary therapy for pain treatment, wherein the subject's androgen serum levels are restored safely and effectively to the middle-upper range of an appropriate reference range. This embodiment of the invention also contemplates the administration of a composition consisting essentially of an androgen to the subject, wherein the subject's androgen serum levels are restored safely and effectively to the middle-upper range of the appropriate reference range.

Alternatively, the invention relates to a method for determining if a human subject would benefit from androgen administration consisting essentially of testing for at least one of a) elevated C-reactive protein, b) elevated erythrocyte sedimentation rate, c) DSM-IV disorder 307.80, d) DSM-IV disorder 307.89, or e) an unresolved stressor state; determining if the subject has androgen levels in the lower half of the appropriate reference range; testing the subject's pain threshold. If the subject has at least one of a) elevated C-reactive protein, b) elevated erythrocyte sedimentation rate, c) DSM-IV disorder 307.80, d) DSM-IV disorder 307.89, or e) an unresolved stressor state, along with androgen in the lower half of the appropriate reference range, and if the subject has androgen levels in the lower half of the appropriate reference range and a low threshold of pain, the subject would be a candidate for androgen therapy. This embodiment of the invention contemplates the administration of a composition either comprising or consisting essentially of a pain threshold increasing amount of an androgen to a human subject having symptoms of androgen deficiency, wherein the subject's androgen serum levels are restored safely and effectively to the middle-upper range of the appropriate reference range.

Doctor's diagnostic kit for patient selection. The invention also relates to a kit for determining if a human subject would benefit from androgen administration as a primary therapy comprising instructions for diagnosing a subject as having an androgen-deficiency related disorder that is treatable by administration of a composition comprising an androgen or by administration of a composition consisting essentially of an androgen. The instructions can comprise instructing a health care provider how to test the subject's androgen serum levels and how to determine if the subject has at least one of the indications defined herein. The instructions can further comprise instructing the health care provider how to testing the subject's pain threshold; and instructing the health care provider to administer an androgen to the subject if the subject has androgen levels in the lower half of the appropriate reference range, a low threshold of pain, and at least one of the indications defined herein; so that the subject's androgen serum levels are restored safely and effectively to the middle-upper portion of the appropriate reference range. The instructions can further direct the health care provider to exclude patients receiving exogenous opioid therapy or include such opioid therapy as an adjunctive, rather than primary, therapy.

Selection of patients. Patients will be selected based on 1) their testosterone serum levels being in the lower half of the reference range, concomitant with at least one of the following: 2a) the presence of chronic or acute unresolved pain (pain assessment as defined elsewhere in this application), and/or 2b) the lack of a feeling of well-being combined with a low threshold of pain (threshold testing as defined elsewhere in this application), and/or 2c) a failure to adapt to or resolve stress (stressors as defined in this application as a maladaptive and unresolved state of "distress"). A medical doctor can either 1) use a diagnostic kit for patient selection, or 2) continue the treatment of someone already diagnosed as having testosterone serum levels in the lower half of the reference range, and with unresolved pain or distress or abnormally low pain threshold, such that continuation treatment is independent of the diagnostic kit for patient selection.

To aid doctors in assessing an individual for treatment, they may consider the symptoms of androgen deficiency. An androgen-deficient subject generally will exhibit a variety of symptoms, including, but not limited to, unresolvable pain, a loss of a feeling of well-being, hot flashes, sweating, insomnia, nervousness, irritability, tiredness, loss of motivation, short-term memory problems, declining self-esteem, depression, decreased energy levels, decline or loss of libido, diminished muscle mass, hair loss, abdominal obesity. In men, a reduced volume of semen and poor erectile function can be symptoms of androgen deficiency. The subjects that receive primary androgen treatment may or may not also be receiving concurrent adjunctive administration of an exogenous opioid. As used herein, the term "concurrently" means sufficiently close in time to produce a combined effect (that is, concurrently may be simultaneously, or it may be two or more events occurring within a short time period before or after each other).

Alternatively, the invention relates to a kit for determining if a human subject would benefit from androgen administration comprising instructions for diagnosing a subject as having symptoms of an androgen-deficiency treatable by administration of an androgen. The instructions consist essentially of instructing a health care provider how to test the subject's androgen serum levels; instructing the health care provider to determine if the subject has at least one of a) elevated C-reactive protein, b) elevated erythrocyte sedimentation rate, c) DSM-IV disorder 307.80, d) DSM-IV disorder 307.89, or e) an unresolved stressor state; instructing the health care provider how to test the subject's pain threshold; and instructing the health care provider to administer a composition either comprising or consisting essentially of an androgen to the subject if the subject has androgen levels in the lower portion of the of the appropriate reference range, has a low threshold of pain, and at least one of a) elevated C-reactive protein, b) elevated erythrocyte sedimentation rate, c) DSM-IV disorder 307.80, d) DSM-IV disorder 307.89, or e) an unresolved stressor state; so that the subject's androgen serum levels are restored to the middle-upper range of an appropriate reference range.

Administration of testosterone can increase the level of endogenous opioid peptides. The invention also relates to a method of increasing endogenous opioid peptide production an androgen-deficient, opioid peptide-deficient human subject comprising: diagnosing a human subject to have at least one of a) elevated C-reactive protein, b) elevated erythrocyte sedimentation rate, c) DSM-IV disorder 307.80, d) DSM-IV disorder 307.89, or e) an unresolved stressor state; determining if the subject has androgen levels in the lower half of the appropriate reference range; determining if the subject low endogenous opioid peptide levels; and, if the subject has at least one of a) elevated C-reactive protein, b) elevated erythrocyte sedimentation rate, c) DSM-IV disorder 307.80, d) DSM-IV disorder 307.89, or e) an unresolved stressor state, along with androgen levels in the lower half of the appropriate reference range and low endogenous opioid peptide levels; administering a composition comprising an androgen to a human subject with androgen and endogenous opioid peptide deficiencies, wherein the subject's production of endogenous opioid peptides is increased. The level of a subject's endogenous opioid peptides can be measured in cerebrospinal fluid, however, one of ordinary skill in the art would know how to test for endogenous opioid peptides at other sites including, but not limited to, the periphery. Further, one of skill in the art might also test for other indicators of pain or efficacy in the cerebrospinal fluid. This embodiment of the invention also contemplates the administration of a composition consisting essentially of an endogenous opioid peptide-increasing amount of an androgen to a human subject having symptoms of androgen deficiency, wherein the subject's levels of endogenous opioid peptides are increased safely and effectively.

Alternatively, the invention relates to a method of increasing endogenous opioid peptide production an androgen-deficient, endogenous opioid peptide deficient human subject consisting essentially of diagnosing a human subject to have at least one of a) elevated C-reactive protein, b) elevated erythrocyte sedimentation rate, c) DSM-IV disorder 307.80, d) DSM-IV disorder 307.89, or e) an unresolved stressor state; determining if the subject has androgen levels in the lower half of the appropriate reference range; determining if the subject has low endogenous opioid peptide levels. If the subject has at least one of a) elevated C-reactive protein, b) elevated erythrocyte sedimentation rate, c) DSM-IV disorder 307.80, d) DSM-IV disorder 307.89, or e) an unresolved stressor state, along with androgen levels in the lower half of the appropriate reference range and low endogenous opioid peptide levels; the method includes administering a composition comprising an androgen to a human subject with androgen and opioid peptide deficiencies, wherein the subject's production of endogenous opioid peptides is increased. This embodiment of the invention also contemplates the administration of a composition consisting essentially of an endogenous opioid peptide-increasing amount of an androgen to a human subject having symptoms of androgen deficiency, wherein the subject's levels of endogenous opioid peptides are increased safely and effectively Opioid peptides are a class of peptide molecules that function as neurotransmitters. Endogenous opioid peptides can be produced at sites within the central nervous system, including but not limited to, the pituitary gland, the hypothalamus, and the spinal cord. Endogenous opioid peptides can also be produced within the periphery. These endogenous opioid peptides resemble exogenous opioid compounds in their actions. The opioid peptides that can be used in the instant invention include, but are not limited to enkephalins. endorphins, dynorphins, adrenorphin, amidorphin, and opiorphin. Each of these subgroups of opioid peptides also has several members. For example, the endorphins include, but are not limited to, alpha-endorphin, beta-endorphin and gamma-endorphin. Enkephalins include but are not limited to, the active forms of enkephalin ala(2)-MePhe(4)-Gly(5), enkephalin D-Penicillamine(2,5), enkephalin leucine, and enkephalin methionine. Other opioid peptides include prooiomelanocortin (POMC), the gene for which codes for beta-endorphin and gamma-endorphin. As with exogenous opioid compounds, the endogenous opioid peptides bind to opioid receptors to exert their action. Pharmacological studies have shown that there are several subtypes of opioid receptors to which the opioid peptides can bind. For example, mu1, mu2, kappa1, kappa2, delta1, delta2 opioid receptors are among those that have been studied. Opioid peptides, as defined herein, include those opioid peptides that bind to these opioid receptors and thereby mediate pharmacologic activity.

For each of the above embodiments of the present invention, additional parameters can be determined. For example, one measurement of an indication that can be treated using an androgen composition includes measuring the level of a subject's endogenous opioid peptides, and if they are decreased below the normal level or reference range, the subject may be a candidate for treatment, if the other conditions of androgen deficiency or symptoms thereof are met. Another indication that can be measured is Substance P, and if the subject's Substance P level is increased above the normal level, the subject may be a candidate for treatment, if the other conditions of androgen deficiency or symptoms thereof are met.

In accordance with the invention, androgen therapy is the primary therapy to be administered for all of the above embodiments of the invention. Further, in accordance with the invention, subjects receiving primary androgen therapy may also receive adjunctive opioid therapy if they have exogenous opioid-induced hypogonadism or other conditions that might require such adjunctive opioid therapy in addition to the primary androgen therapy. Further, while androgens remain the primary therapy for the methods of the invention, other compounds, such as, but not limited to, antidepressants may also be administered as adjunctive therapies.

Thus, using all of the above parameters, one of skill in the art can design and implement a "personalized" treatment program for subjects in need of pain reduction or an increase in their pain threshold. Specifically, one or more kits can be designed to measure and/or test for the levels of a variety of metabolic functions and/or compounds that are important for such functions. For example, not only can the serum levels of androgens, such as, but not limited to, testosterone, be determined, but the level and activity of enzymes that catabolize androgens can be determined. Endogenous opioid peptides, such as enkephalins, can be measured, as can Substance P, an important marker for inflammatory pain. By determining the level of these various metabolic compounds and components, androgen therapy can be modulated and adjusted, depending upon the needs of the specific patients. The adjustment can depend upon the catabolic breakdown and saturation of androgens and their receptors. Further, by adjusting the level of androgen administered as a primary therapy, adjunctive therapies, such as opioids or antidepressants can be adjusted downwards, thus avoiding some of the detrimental side effects of these treatments. As another example, a personalized medicine kit could consist of assessing the activity of enzymes that catabolize testosterone and other endogenous androgens, which could be assessed by targeted gene expression array profiling of these enzymes to determine if an individual has high catabolic activity, necessitating higher dosing of testosterone therapy for efficacy, or low catabolic activity, necessitating lower dosing of testosterone therapy for safety. Likewise, an individual can be tested for endogenous enkephalins over time to determine whether the testosterone dosing is sufficient (enkephalins are raised into the normal range) or dosing needs to be increased (enkephalins have not yet been raised into the normal range). Substance P can be tested, and if its level is decreased to a normal resting state, the testosterone dose can be held constant, or even decreased if there are signs of androgen excess; and if Substance P levels are not decreased, the testosterone dose can be increased to a safe level that is still within the testosterone reference range. One of skill would know whether to test for levels of these molecules in the spinal cord or the periphery, and whether to test cerebrospinal fluid or serum.

Stress and pain are normally closely associated with immunologic mediators of pain. One method of determining the presence of chronic inflammatory pain, is the erythrocyte sedimentation rate, or "sed rate," as described above. Patients with chronic inflammatory pain most often show an elevated sed rate, which is demonstrative of the role of immunologic mediators. A second test for a chronic inflammatory pain state, the C-reactive protein test, can also be used to distinguish chronic inflammatory pain from non-inflammatory pain. Inflammatory states will cause an increase in the level of C-reactive protein, while conditions not related to an inflammatory component would remain unchanged. For purposes of selecting patients with chronic inflammatory pain for treatment, patients can be selected who have an abnormal erythrocyte sedimentation rate test result of >22 mm/hr for men or >29 mm/hr for women, and/or an abnormal C-reactive protein test result of >3 mg/dL, indicating the patient has inflammatory pain. In addition, Substance P, a neurokinin peptide, is also a marker for inflammatory pain. Thus testing a subject for the presence, absence, and/or level of Substance P is another method that can be used to diagnose a chronic inflammatory pain state.

For accruing female patients who are in the lower half of the reference range, either total testosterone, free testosterone and/or bioavailable testosterone can be considered. When considering total testosterone, the "lower half of the reference range for total testosterone" is defined as less than or equal to about 0.5 ng/mL when using the DSL total testosterone serum level assay; or less than or equal to about 0.4 ng/mL when using the Mayo Medical Labs total testosterone serum level assay (Table 1). A person of skill in the art would understand that he would be able to use other equivalent assay tests to define and test for the lower half of the reference range.

For accruing male patients who are in the lower half of the reference range, "lower half of the reference range for total testosterone" is defined as less than or equal to about 6 ng/mL when using the Mayo Medical Labs total testosterone serum level assay. If using another test with its own reference range, a person of skill would assess patient accrual serum level limits in an equivalent way for males vs. females using the appropriate reference range.

The methods of administering androgen therapy. This invention relates to a method of treating a human subject with clinical symptoms of androgen deficiency, chronic inflammatory pain, or unresolvable states of distress, whose serum levels of androgen are in the lower half of the appropriate reference range. The method is comprised of administering a composition comprising a pain-reducing amount of an androgen to a human subject as the primary therapy, such that the resultant serum levels are raised sufficiently for efficacy, but are not raised significantly above the upper end of the reference range. The invention further relates to a method of increasing the pain threshold of an androgen-deficient human subject with clinical symptoms of androgen deficiency, or unresolvable states of distress, whose serum levels of androgen are in the lower half of the appropriate reference range, comprising administering a composition comprising a pain threshold-increasing amount of an androgen as the primary therapy, such that the resultant serum levels are raised sufficiently for efficacy, but are not raised significantly above the upper end of the reference range. The administration can be on a daily basis, or any basis including, but not limited to, weekly or monthly, depending upon the individual patient. The subject of the instant invention may be a female subject or a male subject. The pain to be treated can be caused by a number of circumstances, and further exacerbated by additional stressor(s) introduced into a subject's life. Further, a subject may have a chronic medical state accompanied by an additional stressor state, that causes or exacerbates chronic pain. A stressor state, defined elsewhere herein, may sometimes be the cause of chronic pain in a subject, and/or the subject may be susceptible to stress/distress due to too-low androgen levels. The composition can also consist essentially of an androgen. The androgen can be a biologically active androgen, and can be administered by a variety of means, including, but not limited to, transdermal administration, oral administration, buccal administration, injection, implanted pellets, or suppository.

For example, in some instances (for both males and females) it will be desirable to administer a first bolus dose of the androgen composition, after which a maintenance dose will be administered. The maintenance dose can be determined by measuring the serum androgen levels at predetermined time points to ensure that steady state serum levels are reached and that these levels are maintained within the appropriate reference range. Should the serum androgen levels change over time, the maintenance dose can be altered accordingly. Alternatively, the androgen composition can be administered as a once daily dose, or a divided dose. For example, the composition can be administered twice a day (e.g., morning and evening), three times a day (e.g., with meals), or using any other regimen. Again, the subject's serum androgen levels should reach steady state, be maintained within the appropriate reference range, and can be adjusted over time. Further, in each embodiment of the present invention it is desirable to measure a subject's androgen blood levels at appropriate intervals while the subject is receiving androgen therapy. By doing so, it can be determined if steady state androgen serum levels are attained and the treatment is effective. Further, other longer acting methods of administration of the androgen composition can be considered, including but not limited to, depot formulations, intramuscular injections, and subcutaneous injections, as described herein. Thus, the dose and/or dosing regimen can be altered in the case of a change in a subject's health status (either positive or negative), so as to re-attain the steady state and androgen serum levels within the appropriate reference range. Alternatively, the levels of endogenous opioid peptides or Substance P can also be monitored, and the dose and/or dosing regimen altered as necessary, to ensure that the appropriate levels of endogenous opioid peptides or Substance P are maintained.

In one embodiment of the invention, the biologically active androgen may be a testosterone ester such as, but not limited to, testosterone enanthate or testosterone cypionate. In another embodiment of the invention, the bioactive androgen is testosterone. As described above, this is applicable to treating chronic pain in a subject and/or for increasing the pain threshold in a subject.

The invention relates to a method of reducing chronic pain in a human subject with symptoms of androgen deficiency, androgen-deficiency as defined herein, comprising administering a pain-reducing amount of an androgen as primary therapy to a human subject with symptoms of androgen deficiency, wherein pain is reduced safely and effectively. The subject can be suffering from a condition selected from the group consisting of chronic pain, and pain caused by a chronic stressor state, stressor state as defined herein. The method also relates to a method of increasing the pain threshold in an androgen-deficient human subject comprising administering a pain-threshold-increasing amount of an androgen as primary therapy to the subject, so that the subject's pain threshold is increased safely and effectively, as defined elsewhere herein.

In addition, the subject's androgen serum levels are restored to serum levels at or below the upper end of the appropriate reference range as defined by the mean of the upper end, plus or minus the standard error of the mean, SEM. In some cases, even an androgen serum level slightly above the reference range is both safe and efficacious, with "safety" defined as being within the standard error of the mean of the upper limit of the appropriate reference range and not causing clinical symptoms of androgen excess. Generally, the androgen used in the invention is a bioactive androgen. Bioactive androgens may be active in their native state, and/or may be a precursor or pro-drug that is metabolized to a bioactive state upon delivery to the subject. The method encompasses the administration of a biologically active androgen, which may be, but is not limited to, testosterone, androstenedione, androstendiol, dehydroepiandrosterone, danazol, fluoxymesterone, oxandrolone, nandrolone decanoate, nandrolone phenpropionate, oxymetholone, stanozolol, methandrostenolone, testolactone, pregnenolone, dihydrotestosterone, methyltestosterone, bioactive androgen precursors, and testosterone esters. If a testosterone ester is administered it may be, but is not limited to, testosterone enanthate or testosterone cypionate. Testosterone can be the androgen employed by the invention.

The methods of the invention can be practiced on both female and male subjects. For female subjects, the bioactive androgen can be transdermally administered in a daily unit dose of about 0.1 mg to about 12.8 mg of the androgen in a pharmaceutically acceptable carrier formulated for daily topical administration as a gel and wherein the gel is formulated to deliver steady state total androgen serum levels without raising free androgen serum levels or twenty-four hour free androgen AUC above the levels required for therapeutic efficacy and safety.

For a male subject, the bioactive androgen can be transdermally administered in a daily unit dose of about 35 mg to about 100 mg of the bioactive androgen in a pharmaceutically acceptable carrier formulated for daily topical administration as a gel and wherein the gel is formulated to deliver steady state total androgen serum levels without raising free androgen serum levels or twenty-four hour free androgen AUC above the levels required for therapeutic efficacy and safety. Thus, chronic pain is reduced and the serum levels of free testosterone can be raised to a level that is below or at the upper part of the reference range (+/−SEM).

Androgens used in human studies—form and delivery. Most trials involving hormone replacement therapy have used derivatives of hormones naturally found in women. These derivatized hormones have been promoted because of their patentability and their extended half-life. Androgens are no exception since the androgen hormone most prescribed for women has been methyltestosterone, where methylation at the C-17 position increases its oral bioavailability. A subset of patients do not tolerate derivatized hormones very well, however. Derivatized compounds are not metabolized normally, and therefore may not be the best candidates for commercialization. Non-derivatized exogenous hormones that are structurally identical to endogenous hormones can have short plasma/serum half-lives that range from 10-100 minutes, however, making oral administration of native hormones problematic. To address these issues, transdermal delivery systems have been developed for testosterone, which provide sustained delivery while minimizing first pass hepatotoxicity, which can be problematic with oral formulations of pharmacotherapeutics. Further, for optimal patient tolerance, transdermal gel delivery also avoids the skin irritation many patients experience with repeated use of a transdermal patch delivery system. However, other forms of androgen delivery are available, each having both benefits and drawbacks.

Maintaining safety while administering androgen therapy by maintaining androgen serum levels within the reference range. For females (or males), administration of an androgen that achieves serum levels outside the reference range can be unsafe. The instantly claimed total testosterone level for females from about 0.9 ng/mL to about 1.4 ng/mL, is an extremely narrow range, even narrower than the reference range as shown in Table 1 below. Levels in excess of the instantly claimed range can cause, for example, hirsutism, acne, permanent changes in voice, emotional changes, and the more serious side effects of heart disease, cancer, and liver disease. Thus, it is important to maintain safety by keeping testosterone serum blood levels within the reference range and avoiding clinical symptoms of androgen excess. And safety must be coupled with efficacy as demonstrated by significantly raising testosterone blood levels from baseline levels in the lower half of the reference range to the upper half of the reference range, while significantly decreasing clinical symptoms of androgen deficiency. Examples of these changes and side effects are discussed below.

It is desirable to maintain a patient's androgen serum levels within the middle to upper portion of the appropriate reference range. If androgens are administered in excess, clinical symptoms of androgen excess can appear. These symptoms can range from annoying to dangerous. Generally, the symptoms of androgen excess include, but are not limited to, excessive and abnormal hirsutism, increased anger, adverse lipid changes, cardiovascular disease, abnormal liver function, weight gain, abnormal fat to muscle mass, acne, alteration of libido, edema, functional and structural liver damage, cancer, permanent changes in voice, emotional or mood changes, and diabetes.

For assessing safety, female patients will be dose-adjusted such that the "upper limit of the reference range for free testosterone" is defined as less than or equal to about 3.3 pg/mL when using the DSL free testosterone serum level assay (Table 1); and less than or equal to about 19 pg/mL when using the Mayo Medical Labs free testosterone serum level assay. If using another test with its own reference range, a person of skill would assess safety serum level limits in an equivalent way.

For assessing safety, male patients will be dose adjusted such that the "upper limit of the reference range for free testosterone" is defined as less than or equal to about 300 pg/mL when using the Mayo Medical Labs free testosterone serum level assay. If using another test with its own reference range, a person of skill would assess safety serum level limits in an equivalent way.

High testosterone levels above the reference range have been shown to result in the harmful effects of testosterone. Females with virilizing ovarian tumors provide a good example. Regnier et al., (2002 J. Clin. Endocrinol. Metab. 87(7): 3074) disclose a case study of a woman having a virilizing ovarian tumor (one that secretes testosterone and results in hyperandrogenism in about 80% of cases), with hirsutism that got progressively worse over time. Her total testosterone level was between 3.9 ng/mL and 7.0 ng/mL, which is well above the reference range for females, Table 1. Once the tumor was removed, her testosterone level returned to normal, the hirsutism subsided, and the hyperandrogenism did not recur.

It has also been shown that women with certain conditions, including breast cancer, have a total testosterone level higher than the reference range for women. For example, it has been shown that post-menopausal breast cancer patients can have a total testosterone level of about 1.55 ng/mL, which is above the reference range. Women with testosterone levels of over 1.55 ng/mL have a four-fold greater chance of developing breast cancer. (Ho et al., Singapore Med. J., 2009, 50(5):513).

Further, female-to-male (FTM) transsexuals, who are dosed on purpose with testosterone such that their serum levels of total testosterone reach male levels, i.e., >300 ng/dL (>3 ng/mL) have been studied for the safety of these levels in these genotypic females. Jacobeit (Eur. J. Endocrinol., 2009, 161:795) discloses dosing females to achieve stable serum total testosterone levels within the eugonadal male reference range of about 620+/−130 ng/dL (6.2+/−1.3 ng/mL) for 36 months. Gooren et al. (J. Sexual Med., 2008, 5:765) teach that the female-to-male transsexuals receiving doses of testosterone at or above the male reference range develop hirsutism and male-like increased risk for cardiovascular disease and diabetes. Bachmann et al. (Fertil. Steril., 2002, 77(4):660) teach that testosterone and other androgens have many detrimental side effects, particularly when administered inappropriately or at too high of a dose. Specifically, testosterone can cause acne, weight gain, excess hair, increased anger, adverse lipid changes, and abnormal liver function. Franke et al. (Clin. Chem., 1997, 43(7):1262) disclose that over-administration of anabolic steroids can cause many health problems, including weight gain, acne, hirsutism, alteration of libido, edema, function and structural liver damage. Gooren further teaches that the risk of testosterone-induced side-effects, including cardiovascular disease and hirsutism, are reversed in female-to-male transsexuals who stop receiving testosterone. Finally, testosterone and other bioactive androgens are Schedule C-III controlled substances under the Anabolic Steroid Control Act and, as such, can be dangerous to over-administer in view of the dangerous side-effects of cancer, liver disease, and cardiac disease.

Administration of androgen therapy to males in a safe and effective manner. For males, administration of dosages that would bring a subject's testosterone levels above the male reference range also results in similar and well-documented health issues, as discussed above, although the reference range for males is on the order of about 10 times higher than that for females.

Free and/or bioavailable testosterone should be maintained at safe serum levels for both men and women. All of the above studies show the difficulty in treating both women and men with testosterone or other bioactive androgens. It is important to make sure that the dosage administered to women and men brings the androgen level to the proper, and claimed, range, or the equivalent safe and effective range based on the detection assay used (see Table 1).

By "safe," it is meant that serum levels are within the standard error of the mean SEM of the upper end of the reference range, and there are no unhealthy clinical symptoms of androgen excess. By "effective," it is meant that 1) androgen therapy raises baseline serum levels from the lower half of the reference range to significantly higher serum levels that are still safe within the reference range, and 2) androgen therapy results in significant clinical improvement. For example, the androgen therapy can raise the serum androgen levels from the baseline to the middle or upper portion of the appropriate reference range, and even slightly higher, so long as the safety profile is maintained. While total testosterone is a factor when considering the serum levels of testosterone, it is the free testosterone that is an indicator of the testosterone that is available for biologic action in vivo. Further, free and bioavailable testosterone generally remain in a constant ratio and are reliable indicators of biologic availability, while SHBG-bound testosterone, which is not bioavailable, varies in response to changes in the total pool (Felig, P. and L. A. Frohman, "Endocrinology and Metabolism" McGraw Hill, 4th edition, 2001, 647).

Testing serum levels of androgens in men and women. The reference ranges for women and men differ by a factor of about ten times. Table 1, below, shows the reference ranges for both women and men, and presents data from two different reference range detection methods (male reference ranges only shown using one testing method). For example, the Diagnostic Systems Laboratories (DSL) reference range for women is about 0.1 ng/mL to about 1.0 ng/mL. The reference range determined using the Mayo Medical Laboratories diagnostic test is from about 0.08 ng/mL to about 0.6 mg/mL. Reference ranges are known to differ slightly depending on the detection kit and method used to measure serum levels. The reference range for men, as calculated using the Mayo Medical Laboratories diagnostic test is about 2.4 ng/mL to about 9.5 ng/mL. It is important to remember that, when comparing serum testosterone reference ranges, one must translate the reference range from one test to another. One of skill in the art would know that diagnostic tests vary in their reference ranges, according to which, and whether, monoclonal antibody (mAb) was used for detection (earlier detection systems such as DSL use a detection mAb), or whether no mAb was used for detection (more recently developed detection systems such as Mayo Medical Labs, which use tandem mass spectrometry for detection instead). Thus, the upper end of a safe total testosterone serum level range would be at about 1.0 ng/dL when using the DSL test, versus about 0.6 ng/dL when using the Mayo Medical Labs test. The upper end of a safe free testosterone range would be at about 3.3 pg/mL when using the DSL test, versus about 19 pg/mL when using the Mayo Medical Labs test. Furthermore, the reference range is only an approximation of what would be the "normal" range in individuals, since the reference range would be skewed downward if the "control" population included significant data from subjects with a deficiency. In current times, in which there are abundant stressors in life, it is highly likely that there will be a significant incidence of androgen deficiencies in the population, resulting in androgen reference ranges whose lower end is skewed downward from what is a healthy lower limit.

TABLE 1

TESTOSTERONE SERUM REFERENCE RANGES

|  | DSL ref range[1] | Mayo ref range[1] |
| --- | --- | --- |
| Female TT[2] (age 40-60 yr) | 0.1-1.0 ng/mL (10-100 ng/dL) (100-1000 pg/mL) | 0.08-0.6 ng/mL (8-60 ng/dL) (80-600 pg/mL) |
| Female BioT (age 20-50 yr) (age > 50 yr unkn) | Not determined. | 0.008-0.100 ng/mL (0.8-10 ng/dL) (8-100 pg/mL) |
| Female FT[2] (pre-menopausal) | 0.0003-0.0033 ng/mL (0.03-0.33 ng/dL) (0.3-3.3 pg/mL) | 0.003-0.019 ng/mL (0.3-1.9 ng/dL) (3-19 pg/mL) |
| % of TT that is BioT |  | 10-17% of TT is BioT |
| % of TT that is FT |  | 3-4% of TT is FT |
| % of BioT that is FT |  | 19-38% of BioT is FT |
| Male TT[2] (age >18 yr) |  | 2.4-9.5 ng/mL (240-950 ng/dL) (2,400-9,500 pg/mL) |
| Male BioT (age 40-49) |  | 0.61-2.13 ng/mL (61-213 ng/dL) (610-2,130 pg/mL) |
| Male % of TT that is FT |  | 2.0-4.8% of TT is FT [~22% of TT is BioT] |
| Male FT |  | 0.09-0.3 ng/mL (9-30 ng/dL) (90-300 pg/mL) |

Abbreviations:
TT = total testosterone (free testosterone + testosterone weakly bound to albumin + testosterone tightly bound to sex hormone binding globulin SHBG);
FT = free testosterone (unbound)
BioT = bioavailable (or bioactive) testosterone (free testosterone + testosterone weakly bound to albumin)
[1]Because reference ranges vary according to the antibody used in the test, the source of reference ranges used for the values in this table is indicated: DSL (Diagnostic Systems Laboratories); Mayo (Mayo Medical Laboratories), a common testing service in hospitals for testing TT, FT and BioT (analysis by tandem mass spec after $AmSO_4$ precipitation). Claims based on the reference range from an antibody detection test such as DSL must be converted to the Mayo Medical Labs reference range, which does not rely on antibody detection of testosterone, in order to make comparisons. The above table can be used for this purpose.
[2]Male testosterone levels are generally on the order of 10x female testosterone levels; Free testosterone is on the order of 1-5% of total testosterone.

For all these reasons, it is desirable for a chronic inflammatory pain patient being treated for androgen deficiency, or clinical symptoms of androgen deficiency, to be monitored for their androgen serum levels, including the levels of testosterone, to maintain serum levels safely within the SEM of the upper limit of the reference range that is specific and appropriate for males vs. females. This is true for both men and women, even though the testosterone reference range for men and women differ by about 10-fold. Conversely, it is desirable for a chronic inflammatory pain patient, or a patient being treated for clinical symptoms of distress, as described herein, who is being treated for androgen deficiency, or clinical symptoms of androgen deficiency, to raise their serum levels significantly from their baseline level towards/into the upper end of the reference range to achieve clinical efficacy.

For the purpose of this instant invention, chronic pain, as is normally considered within the clinical arena, is inflammatory pain and is distinct from the non-inflammatory tender point muscle pain of fibromyalgia. The chronic inflammatory pain group of patients (having pain for at least three months, or with unresolvable pain) can be screened for androgen serum levels. Patients to be treated will present an androgen serum level in the lower half of the appropriate reference range.

When considering the low pain threshold group of patients, this includes those patients with substantial stress that cannot be resolved through coping or adaptation (i.e., stress becomes distress). These patients would be likely to have clinical signs or conditions of stress, as discussed herein. Or they could have clinical signs, for example a lack of feeling of well-being or a low libido (lacking the ability to enjoy life), that suggest a high risk of more overt symptoms of clinical distress. The serum androgen levels can be checked and if found to be in the lower half of the appropriate reference range, these patients can also be checked for a low pain threshold using a dolorimeter (or other appropriate measurement system or metric). A low pain threshold correlated with serum androgen levels in the lower half of the appropriate reference range would constitute the group of patients to be treated.

Generally, patients as described above can be stratified by lower half of androgen (or testosterone) reference range and low threshold of pain versus those patients having serum levels in the upper half of the reference range and a normal threshold of pain. The first group are candidates for treatment according to the methods of the invention. Those in the second group should not be treated by these methods, or they can be used in a placebo arm.

Drawbacks to current therapeutics such as anti-depressants for treating chronic inflammatory pain in the clinic. Doctors have begun to employ anti-depressants, as well as cognitive behavioral therapy, for the treatment of pain. For example, serotonin-norepinephrine reuptake inhibitors (SN-RIs), such as duloxetine, and selective serotonin reuptake inhibitors (SSRIs), such as fluoxetine and sertraline, and the tricyclic class of antidepressants can be useful for treating pain. Unfortunately, patients undergoing therapy with these pharmaceuticals can suffer from either a lack of efficacy and/or unintended side effects that are frequently worse than the benefits, such as sexual side effects (e.g., arousal disorder and difficulty achieving orgasm), as well as an FDA mandated black box warning for increased risk of suicidality. Other common side effects of these drugs are nausea, ejaculation failure, insomnia, dizziness, tremor, and decreased libido, as well as exhaustion of testosterone concentrations due to anti-depressant drug treatment.

Numerous clinical states relate to decreased androgen levels and thus to a high risk for chronic pain and chronic stressor states. The treatment disclosed herein can alleviate any of these conditions and further alleviate problems caused by other therapeutics, wherein the conditions and therapeutically-induced problems relate to or cause decreased or low testosterone. There are several chronic conditions that affect T levels directly. Some chronic medical conditions and illnesses will affect and/or decrease testosterone levels directly. For example, orchidectomy or bilateral oophorectomy (surgical removal of testes or both ovaries) can decrease testosterone levels by as much as 50%. Low testosterone levels are also associated with hypothalamic, pituitary, and/or adrenal insufficiency. Hypopituitarisms of any cause, including, but not limited to, Sheehan's syndrome, and adrenal disease, including Addison's disease, can cause low testosterone levels. Finally, chronic illnesses including, but not limited to, anorexia nervosa, clinical depression, advanced cancer, and burn trauma are also causative of low testosterone concentrations. Of note, advancing age is also associated with reduced levels of testosterone and its precursors, DHEA and androstenedione. This likely is caused by natural aging of the ovaries/testes and adrenal glands.

Drugs given to subjects systemically can also cause decreased testosterone levels. Examples of pharmaceutical agents that can cause decreased testosterone levels include, but are not limited to, systemic glucocorticoids or oral estrogens. The decreased levels of testosterone are associated with the suppression of adrenocorticotropic hormone levels with glucocorticoid use and luteinizing hormone levels with oral estrogen therapy. Oral estrogen users have significantly lower levels of free testosterone, due to increased levels of sex hormone-binding globulin (SHBG). Both hyperthyroidism and excessive thyroid medication also increase SHBG levels, which lead to lower levels of free testosterone. In these cases, both the conditions and the treatments can cause lower levels of testosterone.

Other pharmacological agents that can lower testosterone directly include, but are not limited to, trazodone, imipramine, muscle relaxants, analgesics (e.g., non-steroidal anti-inflammatory drugs (NSAIDS), COX-2 inhibitors (e.g., celecoxib, tramadol), sleep medications (e.g., zolpidem, alprazonam), barbiturates, sedatives, clonidine, methyldopa, spironolactone (which has antiandrogenic properties), and selective androgen receptor modulators (SARMs). Further, drugs that otherwise ablate selective portions of pathways involved in effecting androgen responses, also affect testosterone serum levels. These drugs include, but are not limited to, competitive inhibitors of 5-alpha reductase (the enzyme that converts testosterone to dihydrotestosterone) (e.g., finasteride, dutasteride), gonadotropin-releasing hormone (GnRH) agonists (e.g., goserelin, which deprives tumors of testosterone, leuprolide, buserelin, naferelin, deslorelin), GnRH antagonists (e.g., cetrorelix, abarelix, ganirelix, degarelix), anti-androgens that bind to androgen receptors as an antagonist (e.g., bicalutamide, flutamide, both used to treat prostate cancer), corticosteroids (e.g., cortisol, aldosterone, cortisone, prednisone, dexamethasone, triamcinolone, budesonide), and ketoconazole.

In addition, use of various recreational drugs (e.g., alcohol, marijuana, cocaine, heroin, methadone) can also cause decreases in testosterone and sexual function.

Chronic medical conditions that are treated, for example with anti-depressants, can also be associated with decreased testosterone levels. One set of medical conditions can include, but is not limited to, medical conditions being treated with certain medications, especially antidepressants. Specific indications might be decreased sexual function in both men and women. Such indications include psychosocial issues and psychological disorders (including, but not limited to, depression and anxiety), physiological/medical conditions (including, but not limited to menopause, age-related sexual drive decline, and fatigue). Another set of medical conditions that might be treated with antidepressants includes all forms of chronic illnesses (including, but not limited to cardiovascular disease, diabetes mellitus, arthritis, renal failure and cancer. Gynecological and/or breast cancer can be particularly causative of such problems).

Patients exhibiting the aforementioned conditions, which also have a component relating to a low sex drive and/or low testosterone levels can be treated by a variety of pharmacological agents. For example, depression and anxiety can be treated with any one of a number of agents, including but not limited to, tricyclic antidepressants (e.g., amitriptyline, clomipramine, butriptyline, doxepin), selective serotonin reuptake inhibitors (SSRIs) (e.g., fluoxetine, sertraline, citalopram, paroxetine), serotonin-norepinephrine reuptake inhibitors (SNRIs) (e.g., duloxetine, venlafaxine, desvenlafaxine), anxiolytics and antipsychotics (e.g., antidepressants, antihistamines, benzodiazepines, azaspirones), and beta blockers (e.g., carvediol, acebutolol, metoprolol, atenolol, timolol, labetolol). Both the conditions treated and the agents used to treat these conditions can decrease testosterone levels, exacerbating the androgen deficiency, or symptoms thereof.

The instant invention can be used as a primary therapy and concurrently with the aforementioned pharmacological agents, and can counteract the decreased sexual function and low levels of testosterone resulting from the conditions being treated, as well as the pharmacological agents being used to treat those conditions.

Although caused at least in part by the stress ("distress," using Selye's terms) of disease and illness, the detailed precipitating mechanism of testosterone decrease is not well defined. However, the descriptions presented here go a significant way toward providing a coherent overview that is strongly supported by the data pulled together herein.

As stated above, antidepressants can also be taken as an adjunctive therapy in conjunction with primary androgen therapy. Here, it is likely that the benefits of androgens can work in concert with the benefits of the SNRIs, SSRIs or tricyclic antidepressants. Therefore, the invention further relates to 1) the treatment of pain comprising administering an androgen alone or in combination with an antidepressant, or 2) the treatment of depression as an unresolvable state of distress or combined with a lack of feeling of well-being, comprising administering an androgen alone or in combination with an antidepressant, and 3) when these patients have serum levels of androgen in the lower half of the reference range. The androgen can be those previously described. The antidepressant can be selected from SSRIs or SNRIs including duloxetine, fluoxetine, sertraline, and a tricyclic antidepressant. The dosage of the antidepressant compounds can be the usual range of administration for these compounds. Treatment can be the androgen either alone or in combination with antidepressant compounds.

The Circle Hypothesis provides a mechanistic basis and the overall biologic context or paradigm for a rational treatment of clinical symptoms of androgen deficiency. The underlying circle hypothesis, as described above, applies to both the chronic pain, and/or the abnormally low pain threshold patient populations comprised of patients in a state of distress or lacking a feeling of well-being. Using the information gleaned from the testing protocols, one can appropriately select the patients for androgen therapy.

Methods for evaluating and treating subjects. The invention, therefore, also relates to a method of determining if a subject should be treated with androgen therapy. Such a method can comprise testing a subject for androgen serum levels; testing the subject for the subject's pain threshold, wherein if the subject has low androgen serum levels and a low threshold of pain or clinical evidence or symptoms of androgen deficiency as defined elsewhere, an androgen is administered to the subject.

In one embodiment of the invention, the bioactive androgen may be a testosterone ester such as, but not limited to, testosterone enanthate or testosterone cypionate. In another embodiment of the invention, the bioactive androgen is testosterone. As described above, this is applicable to both the method of treating chronic pain in a subject and the method of increasing the pain threshold in a subject.

Female dose. In one embodiment of the invention, and for both the method of treating chronic pain in a female human subject and the method of increasing the pain threshold in a female subject, the androgen can be administered in a unit dose of about 0.1 mg to about 12.8 mg of the androgen. In one embodiment, the androgen can be formulated as a transdermal preparation in a pharmaceutically acceptable carrier formulated for daily topical administration as a gel and wherein the gel is formulated to deliver steady state total androgen serum levels without raising free androgen serum levels or twenty-four hour free androgen AUC above the levels required for therapeutic efficacy and safety. Preferably, the daily unit dose of the androgen is from about 1.0 mg to about 12.8 mg. More preferably, the daily unit dose of the androgen is from about 2.5 mg to about 10.0 mg. Even more preferably, the daily unit dose of the androgen is from about 3.2 mg to about 9.6 mg. Most preferably, the daily unit dose of the androgen is from about 6.0 mg to about 8.0 mg. The daily unit dose of the androgen can be about 6.5 mg or about 7.5 mg.

In another embodiment, the dosing range can be incremental. For example, the dose to be administered to a female subject can be about 2.5 mg; 5.0 mg; 7.5 mg; or 10.0 mg. In order to determine the most appropriate dosage for a particular subject, a physician may start the patient on a low dose, and titrate the dose upwards until a dose that is both effective and safe is reached. In yet another embodiment, the incremental dosage rate can start at 3.2 mg, and rise progressively to 6.4 mg, 9.6 mg, and 12.8 mg, using a 0.8% gel formulation. For example, and in the case of a transdermal preparation, patients can be started with 2 packets of 0.8% testosterone or placebo gel per day for the first four weeks. Each packet can contain 400 mg of 0.8% testosterone gel (3.2 mg testosterone, to deliver 10% or 320 µg bioavailable testosterone) or 400 mg placebo gel in it. After four weeks, any patient who tests >3.3 pg/mL for serum free testosterone (testosterone serum levels above the DSL reference range), can decrease the dose by one gel packet/day. Any patient who tests ≤1.9 pg/mL for serum free testosterone (within or below the lower half of the DSL testosterone reference range) can increase the dose by one gel packet/day until the serum level is raised to between about the mid-range and the upper end of the reference range+/−SEM. It is the level of free testosterone and/or bioavailable testosterone, rather than total testosterone, that is important to maintain within the reference range+/−SEM, since it is free testosterone or bioavailable testosterone that correlates tightly with safety.

In one embodiment of the invention, the daily unit dose can be delivered via a transdermal gel having about 0.1% to about 10.0% of the androgen. Preferably, the transdermal gel can have about 0.5% to about 5.0% of the androgen. More preferably, the transdermal gel can have about 0.5% to about 2.5% of the androgen. Most preferably, the transdermal gel can have about 0.8-1.0% of the androgen.

The daily unit dose of the androgen can be from about 4.0 mg to about 10.0 mg, or from about 6.0 mg to about 8.0 mg. At 10% bioavailability for the androgen in the gel that is actually delivered to the blood, the daily unit dose-to-be-delivered of the androgen can be from about 0.4 mg to about 1.0 mg, or from about 0.6 mg to about 0.8 mg androgen.

The formulation of the invention will preferably be used at a unit dose of 800 mg gel of 0.8% testosterone (6.4 mg testosterone), and then, depending on serum levels at 4 weeks, adjusting down to 400 mg gel of 0.8% testosterone (3.2 mg testosterone), or adjusting up to 1200 mg gel of 0.8% testosterone (9.6 mg testosterone), to maintain the unit dose to achieve safe and effective serum levels.

Alternatively, testosterone can be administered to females in a variety of different ways, including, but not limited to injection, oral administration, buccal administration, implanted pellets, or suppositories. If an alternate method of administration is chosen for females, the regimen of administration may also be varied, as described herein. Androgen serum level targets for females. In another embodiment of the invention, and for both the method of treating chronic pain in a subject and the method of increasing the pain threshold in a female human subject, the daily unit dose of the androgen may be selected to maintain steady state total androgen serum levels within a range of between about 0.7 ng/mL and about 1.6 ng/mL, and preferably between about 0.9 ng/mL and about 1.4 ng/mL for at least 24 hours after administration without raising free androgen serum levels or twenty-four hour free androgen AUC above the levels required for therapeutic efficacy and safety, as defined elsewhere herein. Further, the free androgen serum levels and twenty-four hour free androgen AUC should not be raised above levels required for therapeutic efficacy and safety. Specifically, the free androgen serum levels can be raised to between about 1.00 pg/mL and about 3.3 pg/mL+/−2 SEM. (About 3.3 pg/mL using the DSL test is equivalent to about 19 pg/mL using the Mayo Medical Labs mass spectrophotometry method of measuring free testosterone, Table 1. The upper end of the reference range is determined by which method of measuring free testosterone is used). The twenty-four hour free androgen AUC levels can be raised to between about 35.18 pg-h/mL and about 72.60 pg-h/mL; more preferably the free androgen serum levels can be raised to between about 2.00 pg/mL and about 3.3 pg/mL and the twenty-four hour free androgen AUC levels can be raised to between about 40 pg-h/mL and about 65 pg-h/mL. For a postmenopausal woman with clinical symptoms of androgen deficiency, the full reference range of the premenopausal woman can be used to determine the optimal desired serum testosterone level.

Male dose. In yet another embodiment of the invention, and for both the method of treating chronic pain in a male human subject and the method of increasing the pain threshold in a male human subject the androgen is administered in a unit dose of about 35 mg to about 100 mg of the androgen. In one embodiment, the androgen can be formulated as a transdermal preparation in a pharmaceutically acceptable carrier formulated for daily topical administration as a gel. Further, the gel is formulated to deliver steady state total androgen serum levels without raising free androgen serum levels or twenty-four hour free androgen AUC above the levels required for both therapeutic efficacy and safety.

In one embodiment of the invention, the daily unit dose of the androgen for a male can be from about 50 mg to about 90 mg/day or from about 65 mg to about 85 mg. Alternatively, the daily unit dose of the androgen can be about 75 mg or about 80 mg. In one embodiment, as exemplified here, the unit dose above can be administered as a once-a-day daily unit dose of a transdermal gel, whereby steady state serum androgen levels are reached within 24 hours. Alternative formulations and dosing can be used as discussed herein, although the preferred embodiment is a formulation that holds to the safe delivery of "not-too-much-too-fast" testosterone, i.e., without unsafe spiking while raising blood levels above baseline to achieve clinical efficacy, and a delivery rate that achieves steady state within days of initiating therapy. For other routes of administration, the dosage can be easily varied by one of ordinary skill in the art. Ultimately, the safe and effective reduction of pain and the concomitant desired serum levels of the androgen can be obtained using varied routes of administration and varied dosage levels, which can be determined on a case-by-case basis.

In another embodiment, the dosing range can be incremental. For example, the dose to be administered to a male subject can be about 50 mg; 75 mg; 80 mg; or 90.0 mg. In order to determine the most appropriate dosage for a particular subject, a physician may start the patient on a low dose, and titrate the dose upwards until a dose that is both effective and safe is reached. In yet another embodiment, the incremental dosage rate can start at 50 mg, and rise progressively to 70 mg, 80 mg, and 90 mg. In the case of a transdermal preparation, patients can be started with an appropriate number packets of a testosterone gel formulated for males by one of ordinary skill in the art or placebo gel per day for the first four weeks. Each packet can contain the appropriate amount of a testosterone gel or the corresponding placebo gel. After four weeks, any patient who tests above the appropriate male reference range for serum free testosterone, can decrease the dose over time until the appropriate reference range is reached and maintained. Any patient who tests at or below the lower half of the male reference range for serum free can increase the dose over time until the serum level is raised to between about the mid-range and the upper end of the reference range+/−SEM. As above, it is the level of free testosterone and/or bioavailable testosterone, rather than total testosterone, that is important to maintain within the reference range+/−SEM, since it is free testosterone or bioavailable testosterone that correlates tightly with safety.

In one embodiment of the invention, the daily unit dose can be delivered via a transdermal gel having about 0.1% to about 10.0% of the androgen. Preferably, the transdermal gel can have about 0.5% to about 5.0% of the androgen. More preferably, the transdermal gel can have about 0.5% to about 2.5% of the androgen. Most preferably, the transdermal gel can have about 0.8-1.0% of the androgen.

Alternatively, testosterone can be administered to males in a variety of different ways, including, but not limited to injection, oral administration, buccal administration, implanted pellets, or suppositories. If an alternate method of administration is chosen for males, the regimen of administration may also be varied as described herein.

Androgen serum level targets for males. The daily unit dose of the androgen for a male can be selected to maintain steady state total androgen serum levels within a range of between about 2.4 ng/mL to about 9.5 ng/mL for at least 24 hours after administration. In addition, the free androgen serum levels and twenty-four hour free androgen AUC should not be raised above the levels required for therapeutic efficacy and safety, as defined elsewhere herein. Specifically, the free androgen serum levels can be raised to between about 90 pg/mL and about 300 pg/mL and the twenty-four hour free androgen AUC levels can be raised to between about 350 pg-h/mL and about 800 pg-h/mL; more preferably the free androgen serum levels can be raised to between about 150 pg/mL and about 300 pg/mL and the twenty-four hour free androgen AUC levels can be raised to between about 400 pg-h/mL and about 700 pg-h/mL. As above, these preferred ranges can be adjusted for the Mayo Medical Labs reference ranges or any other reference laboratory.

In another embodiment of the invention, the unit dose for male subjects can be selected to maintain steady state total androgen serum levels within a range of between about 4.0 ng/mL and about 9.5 ng/mL, preferably between about 6.0 ng/mL and about 9.5 ng/mL, for at least 24 hours after administration without raising free androgen serum levels or twenty-four hour free androgen AUC above the levels required for therapeutic efficacy and safety, as defined elsewhere herein.

Transdermal gel formulations for an androgen and at least one pharmaceutically acceptable carrier. Formulation of transdermal gels are standard and well known in the art, and can contain a wide variety of components, including penetration enhancers. Penetration enhancers have different strengths and can be optimized to obtain the desired transdermal delivery effect. For example, penetration enhancers such as oleic acid and sodium hydroxide are stronger and allow for more and faster delivery of a transdermally-delivered drug and are frequently used in androgen compositions approved for male use. These formulations are based on the idea that inclusion of such male-specific penetration enhancers may help achieve absorption of the relatively high amounts of testosterone that males require. If too potent a penetration enhancer is used, the blood stream can be flooded with drug too fast, resulting in "too-much-too-fast" delivery profiles. In many male formulations, it is apparent that these potent penetration enhancers are being used, because the compositions containing such penetration enhancer components frequently results in a spike in androgen serum levels. Such a spike, usually in the first two hours after administration, can prevent sustained and effective delivery of androgens in both males and females. Further, depot preparations that are sometimes used for males, deliver too much androgen, too quickly. Finally, male transdermal formulations carry a black box warning regarding transmission of the gel from the patient to others in contact with the patients, while depot intramuscular injections risk too-high levels of testosterone initially, with too-low levels at the tail end of the delivery period of time.

Less potent penetration enhancers can be used for a more even drug delivery profile. In addition, transdermal formulations using less potent or no penetration enhancers can be absorbed into the skin at a more even rate without unsafe spiking. Such penetration enhancers are employed for the instant invention and can be used such that unsafe spiking is avoided while robust and safe delivery is achieved, even in males. During transdermal delivery, a portion of the androgen goes directly into the blood stream and a portion of the androgen is absorbed by fatty tissues. Since testosterone and other androgen compounds are hydrophobic, they are retained in the fatty tissue and are released into the bloodstream evenly and over a sustained period of time due to the inherent hydrophobic properties of testosterone residing in the inherent hydrophobic environment of the fatty tissues. Steady state androgen blood levels are reached generally within 24 hours, if not sooner.

In addition, the invention relates to the safe and effective administration of a transdermal composition comprising an androgen to treat chronic pain, to increase the pain threshold of a subject, and to increase production of endogenous opioid peptides in a subject. The composition can also consist essentially of an androgen. The invention further relates to administration of a transdermal composition that significantly and uniquely raises serum levels of the androgen (e.g., testosterone) to a level approximating the upper portion of the appropriate reference range. The invention also relates to administration of an androgen composition as the primary therapy to patients that are either undergoing exogenous opioid treatment as an adjunctive therapy, as well as administration of the androgen composition to patients who are not undergoing concurrent exogenous opioid therapy. Further, other compounds, such as, but not limited to, antidepressants can also be administered as an adjunctive therapy to the primary androgen therapy.

One of skill in the art would be able to derive a formulation appropriate for males or females, and appropriate to attain the required serum androgen levels that are both safe and efficacious. Pharmaceutical handbooks provide a wealth of information to the transdermal composition formulator, and assist the formulator in determining the appropriate composition to obtain the desired drug delivery profile. Texts such as Ansel's Pharmaceutical Dosage Forms and Drug Delivery Systems (eds. Allen, Jr., et al., Lippincott Williams & Wilkins, Philadelphia, 8$^{th}$ Edition, 2005 and Remington: The Science and Practice of Pharmacy (ed. Alfonso R. Gennaro, Lippincott Williams & Wilkins, Philadelphia, 20$^{th}$ Edition, 2000) contain chapters relating to transdermal formulations, and components that might be used therefor. Using such well-known information and techniques, one of ordinary skill in the art would be able to formulate a transdermal androgen composition and to adjust the component type and concentration, so that the resulting serum androgen levels are both safe and efficacious, are within the appropriate reference range, and achieve a steady state within twenty-four hours without a potentially dangerous spike in androgen serum levels. The formulation chosen would improve clinical symptoms of androgen deficiency, pain, and/or distress without causing either unsafe clinical symptoms of androgen excess or an ineffective androgen administration.

The transdermal gel formulation has advantages over current methods, as well as transdermal patch methods, that include 1) steady state within about 24 hours, 2) even delivery over each daily 24 hour period with once-a-day dosing and without over-shooting the upper limit of the reference range, 3) avoidance of delivering too-much-drug-too-fast and the resultant unsafe serum spiking profile over each 24 hour period of time, 4) avoidance of first pass metabolism effect, 5) avoidance of skin irritation seen with some other gels and with the patch, 6) all of which optimize safety and efficacy with respect to raising serum testosterone levels significantly above baseline levels, and with respect to achieving significant clinical efficacy in reducing inflammatory pain or increasing the pain threshold or increasing endogenous opioid peptides without evidence of androgen excess or harmful clinical side effects.

Routes of administration. As will be obvious to those of skill in the art upon this disclosure, other pharmaceutically acceptable androgen therapies can be used, as long as the desired serum androgen profiles are obtained. Effective amounts and routes by which the androgen or combination of androgens can be administered in a safe and effective manner according to the present invention can also be used, and are described herein.

The androgen can be administered transdermally, orally (as an immediate release tablet or capsule, an orally disintegrating tablet or capsule, and enterically coated tablet or capsule, and a delayed release tablet or capsule, or a form of an androgen as a prodrug), by injection (intramuscular, intraperitoneal, intravenous, or subcutaneous); by buccal administration, via an implanted pellet, a dragee or a suppository. One of skill in the art would be able to adjust the dosages delivered by these methods, so that the delivery of the androgen composition to the bloodstream results in the desired safe and efficacious androgen serum levels.

The bioactive androgen can be formulated with a pharmaceutically acceptable carrier. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

For transdermal administration, the formulation can include, but is not limited to, the androgen, a penetration enhancer or excipient, an emulsifier, a gelling agent; a lubricant, a thickening agent, a solvent or co-solvent, emollient, humectant, protein stabilizer, moisturizer, crystallization inhibitor, neutralizing agent, a buffer, an alcohol, and water. Variations of the formulation and routes of administration will be evident to one of skill in the art such that, upon administration of the bioactive androgen, both safe and effective serum levels of androgen are obtained.

For intramuscular, intraperitoneal, subcutaneous and intravenous use, the androgen compositions of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In addition, androgen therapy provides a useful means for alleviating unresolvable pain, both acute and chronic. Chronic pain is defined by neurologists as pain lasting three months or longer. Chronic pain is particularly debilitating, and can be diffuse or localized. Acute pain, or pain lasting less than three months, can likely also be treated with androgen therapy, as long as the acute pain is associated with a concurrent androgen deficiency or symptoms of androgen deficiency. An acute pain appropriate for treatment would likely be related to an unresolvable stress or state of distress and/or an abnormally low threshold of pain.

In a preferred embodiment, the androgen administered as the primary pain therapy is testosterone, an active metabolite of testosterone such as dihydrotestosterone or androstenedione or a testosterone derivative such as methyltestosterone, testosterone enanthate or testosterone cypionate. Examples of available pharmacologic preparations of androgens believed to be useful in this invention include, but are not limited to danazol, fluoxymesterone, oxandrolone, methyltestosterone, nandrolone decanoate, nandrolone phenpropionate, oxymethalone, stanozolol, methandrostenolone, testolactone, pregnenolone and dehydroepiandrosterone (DHEA).

The "Circle Hypothesis." As described in detail above, FIGS. 3A-3B show the proposed metabolic pathway for testosterone in relation to nociception. Other bioactive androgens may also be employed in the treatment of chronic pain. FIGS. 3A-3B show the hypothesized metabolic pathway in normal subjects and subjects with chronic pain. FIG. 3A shows that, in normal individuals, a painful/stressful stimulus upregulates Substance P in nociceptive relay neurons and concurrently serotonin levels drop. This is consistent with a loss of feeling of well-being. Substance P, in turn has been found to stimulate aromatase, which allows for the conversion of testosterone to estradiol within the central nervous system, with subsequent upregulation of opiates and/or enkephalinergics and other pain dampening mediators, with consequent dampening of pain and Substance P. In FIG. 3B, subjects with deficient levels of testosterone are predicted to have a frustrated cycle in which aromatase fails to convert testosterone to estradiol due to the deficiency of androgen, leading to insufficient induction of opiate peptides and/or other mediators to dampen Substance P and nociceptive signals, resulting in abnormal chronic, diffuse, widespread pain, as well as wind-up exacerbation of pain and clinical states of distress. Essentially, when the body is subjected to a painful and/or stressful stimulus, testosterone metabolism is stepped up as a mechanism to cope with and overcome pain. When androgens, such as testosterone, are depleted, which they are under conditions of stress (Opstad, J., 2002, 74: 99-204), then the body's pain-fighting mechanisms break down. Androgen therapy can thus break this frustrated cycle, and alleviate both acute and chronic pain that is exacerbated with androgen deficiency, or symptoms of androgen deficiency.

Example 1

Proof of concept for efficacy and safety of androgen therapy for tender point pain. The fact that it is testosterone rather than estrogen that is the important therapeutic to administer is suggested by the significant decrease in serum-derived free testosterone concentrations (unbound testosterone) that has been documented for premenopausal female fibromyalgia patents relative to healthy volunteers. (Dessein P H et al., 1999 Pain 83: 313). The pharmacokinetics, clinical efficacy and safety of transdermal delivery of androgen hormone for treatment of fibromyalgia in women was previously demonstrated in a phase 1-2 clinical trial (U.S. Pat. No. 7,799,769 B2). The transdermal testosterone gel used for that study was shown to be both safe and clinically effective. The distinct difference between fibromyalgia and the chronic inflammatory pain states in the present invention is evidenced by 1) the different and non-overlapping types of clinicians who normally treat the two types of pain, 2) distinct differences in DSM diagnostic criteria, 3) distinct differences in the genesis of chronic pain and their etiologies (fibromyalgia muscle tender point pain is known to be uniquely non-inflammatory), and 4) distinct differences in symptoms and clinical treatments. For all the reasons mentioned above, an expert knowledgeable in the treatment of chronic inflammatory pain would not think to utilize androgen gel therapy for a chronic inflammatory pain state. This is underscored by the fact that androgen therapy is not currently used to treat any chronic inflammatory pain states in the clinic. Thus, the present invention offers a unique and distinct indication and treatment method. However, the afore-mentioned study shows that a transdermal androgen gel formulation can be used to significantly raise the serum levels of testosterone in women with fibromyalgia safely and in a clinically effective way.

In the study cited in U.S. Pat. No. 7,799,769 B2, testosterone was formulated as a gel and used to treat women with low androgen levels. Pharmacokinetic analysis of the serum testosterone concentration data from these testosterone gel treated patients revealed that mean serum total and free testosterone concentrations were significantly increased from levels in the lower half of the reference range to levels in the upper portion of the reference range in response to therapy. Mean serum concentrations were increased quickly, within a few hours, with steady state being reached within 24 hours, with no unsafe spiking, and maintained to the end of the 28 day time course. Thus, in response to therapy, these increased serum levels equilibrated at steady state and remained at safe levels. Significant clinical efficacy in the treatment of fibromyalgia patients was demonstrated with respect to decreased muscle tender point pain, as well as ablatement of other fibromyalgia-unique symptoms. Symptoms that were not specific for fibromyalgia were not significantly changed. The sum of the tender point tests showed a statistical significance with a p value of 0.012 on day 28 vs. day 1. Tender point examinations (a test designed specifically to measure fibromyalgia-related symptoms) were administered by a qualified rheumatologist experienced in and knowledgeable about the criteria specified by the American College of Rheumatology. It is noted that these patients saw a rheumatologist, rather than a neurologist. A chronic inflammatory pain patient would see a neurologist who has different training and skill sets to treat this condition.

The delivery of drug in a safe manner in women was achieved by taking into account the unique sex steroid hormone physiology of women compared to men. This formulation uniquely provides the correct pharmacokinetic profile women need, raising their total and free testosterone serum levels to clinically effective levels within hours, while not over-shooting safe serum levels—as defined, in part, by maintaining mean free testosterone levels within the upper end of the reference range for women, as well as the avoidance of any clinical symptoms of androgen excess. The strong clinical safety profile included the following components: 1) normal cardiac function, liver function and kidney function after blood panel assessment, 2) clinical assessment showing maintenance of good overall general health in the study patients, 3) no adverse events attributable to the treatment, and 4) no clinical evidence of androgen excess such as hirsutism or unhealthy change in cardiovascular parameters. Others have shown that androgen excess in women, for example female-to-male transgender patients, readily have these symptoms of androgen excess.

Male formulations, by necessity, require excipients or skin permeation enhancers to quickly and effectively deliver the large bolus of androgen that men require for effective clinical treatment. When applied to women, male gel formulations can deliver a bolus of too much testosterone too fast, overwhelming biologic pathways that are uniquely different in female androgen physiology. Such gels can inherently have properties such that they may either be used at too low a volume of gel in order to maintain safety and avoid overshooting the female reference range, or they can be used at an unsafe and too high a volume in order to maintain clinically effective delivery of drug after the early peak of high serum levels, i.e., during the second half of the 24 hour delivery profile when levels are too low to maintain efficacy over the entire 24 hour period.

In summary, Example 1 offers proof of concept that women with decreased androgen levels can receive a transdermal testosterone gel formulation, with a delivery profile designed uniquely appropriate for women that avoids the inherent pitfalls associated with the usage of a male testosterone gel formulation in women. These results, from the standpoints of 1) pharmacokinetic efficacy (the serum levels were significantly raised), and 2) safety (the serum levels were maintained at safe free testosterone reference range levels and there were no clinical or blood panel symptoms of androgen excess) support the functional properties of the tested testosterone transdermal gel formulation to treat individuals with chronic pain. This Example illustrates significant improvement in fibromyalgia-related non-inflammatory muscle tender point pain in patients.

PROPHETIC EXAMPLES

Planned Prophetic Studies

Clinical studies in two different types of patients will be conducted in the future to confirm the effectiveness of androgen therapy to 1) alleviate pain and 2) increase the threshold of pain. Specifically, patients will be examined for reductions in chronic pain and modulation of pain threshold following an improvement in serum androgen levels. The initial drug delivery vehicle will be a gel formulation using a transdermal delivery system androgen that will result in safe and effective serum levels. After initial treatment, serum levels will be monitored in order to maintain levels within the appropriate reference range and avoid adverse effects. A dose resulting in an androgen level above the reference range will be reduced such that a safe and effective dose is maintained. Females will be the first to be studied; males will then be studied with a similar approach. The most likely formulation studied initially will be a 1% or a 0.8% testosterone gel to be administered as a daily unit dose for females. A male formulation to deliver about ten times the amount of active androgen will be tested subsequently. All studies can include an arm wherein the subjects are not undergoing concurrent exogenous opioid therapy.

Prophetic Example 1

Population Study to Screen Subgroups of Pain Patients for Serum Testosterone Levels Patients with various types of chronic or unresolved pain will first be screened for testosterone levels in the lower half of the appropriate reference range. Pain patients will be categorized by gender and may include, but are not limited to, cancer patients, post-surgical patients, accident victims, combat veterans, patients with neuropathy, hyperalgesia, allodynia, depression, and rheumatologic/autoimmune disorders. These subsets of patients will also be stratified by assessment of their clinical symptoms of androgen deficiency. Blood will be taken by venipuncture at the start of treatment and again at each of several specific time points in the study for each of the patient groups. Androgen levels will be determined by a laboratory expert in handling clinical trial samples and testing hormone levels in humans. One skilled in testing for serum levels of the sex steroid hormones, including testosterone, will know standard practices for blood draws. Patient groups will be separated into female and male subsets. Other diagnostic or therapeutic tests will be used as appropriate. A Visual Analog Scale (VAS) pain perceived assessment test is an example of such a test. Blood will be drawn at a common time of day, preferably the peak time for androgens, at 8 AM, after fasting since midnight. Other testing might include total serum hormone levels, free serum hormone levels, serum binding globulins, serum estradiol levels, evaluations of cardiac health, kidney function and liver function, physical function, psychological function, and metrics for restorative sleep. The study physicians will also complete a Physician's Form. Results will be stratified by androgen serum levels and symptoms of androgen deficiency.

Prophetic Example 2

Open Label Testosterone Therapy Study of Patients with Pain

Proof of Concept Study in pain to test efficacy of androgen therapy in patients with pain. One or two of the groups evaluated above will be chosen as a test population for an efficacy study preliminary to larger clinical trials. The initial target will be the group, or groups, of patients with clinical symptoms of pain with the highest percentage of low testosterone screening levels within the lower half of the appropriate reference range. The purpose of the study will be to show the efficacy of open label androgen therapy in one of the groups already tested. The study will be similar in design to the screening study. Evaluations will take place at appropriate times during the study and at the end of the study, be similar to Prophetic Example 1, and will also include baseline data. Patients will be provided with a verbal-anchored VAS form and a patient questionnaire to assess their symptoms and level of pain in a quantitative manner, similar at least in part to Example 1, to demonstrate efficacy of testosterone therapy in treating pain. Conventional statistical analysis will be applied.

Prophetic Example 3

Double Blind Placebo Controlled Study of Patients with Pain

Based on the results of the previous study described above, a larger, and longer, clinical trial will be conducted in the most appropriate subsets of patients. Patients will first be screened for testosterone levels in the lower half of the appropriate reference range. They will then be assigned randomly to one of the following regimens: 1) placebo daily for three months; 2) androgen therapy comprising testosterone or other bioactive androgen for three months. Treatment will be randomized to an active treatment group with pain and a placebo treatment group without pain. An open label extension study may be added as well. While the treatments, the evaluations, and the analyses will be similar to the previous studies, much more specific information will be generated from this study since the study will be larger and longer. Evaluations and testing will be similar to Prophetic Examples 1 and 2.

Prophetic Example 4

Population Study in Patients with Low Thresholds of Pain

Using Prophetic Examples 1-3 as a model, patient populations will be selected based on the above criteria but with a goal of studying individuals with low pain thresholds. Some of these patients will also lack a feeling of well-being combined with a low threshold of pain. Patients with long-standing stressors in their lives as defined by a failure or poor ability to resolve states of stress, or the maintenance of a maladaptive state of "distress," will be tested for levels of free testosterone. Once low androgen levels have been established as being in the lower half of the appropriate reference range, a low threshold of tolerance to pain will be documented before treatment. Patients will be pain threshold-tested or challenged using any of a number of methods, including but not limited to the following: validated motor functional limitations testing coupled with pain assessment (Mannerkorpi et al., 1999 Arthritis Care and Research, 12: 193), application of pressure to specific susceptible tender points of the skin by a dolorimeter coupled with VAS pain scoring (standard rheumatologic assessment technique), or the application of controlled increases in pressure stimuli by hydraulic piston to the left thumbnail coupled with VAS pain scoring (Gracely et al., 2002 Arthritis & Rheumatism 46: 1333). Additional methods of evaluating pain and discomfort may include, in addition to the previous pain threshold testing, the SF-36 Health Survey, metrics for physical function and psychological function, and/or other similar validated instruments and metrics. Thus, an open label population study will be conducted in patients with one of many longstanding stressors, whose testosterone levels are shown to be in the lower half of the appropriate reference range, and whose pain threshold is low. Androgen therapy will then be utilized to safely and effectively increase the patient's testosterone level to show significant improvement in the low pain threshold.

Prophetic Example 5

Open Label Testosterone Therapy Study of Patients with Low Thresholds of Pain

Subsequent to the population study, a Proof of Concept Study will follow. It will be a study similar to the Population Study, and will follow a protocol similar to Prophetic Example 2. One of the groups evaluated above will be chosen as a test population for an efficacy study preliminary to larger clinical trials.

Prophetic Example 6

Double Blind Placebo Controlled Study of Patients with Low Thresholds of Pain

Subsequent to the Proof of Concept Study, a blinded placebo controlled study will follow. It will be a study similar to the Proof of Concept Study and will be a larger, and longer, clinical trial based on the results of the previous study in one of the various subsets of patients with an increase threshold of pain. This study will follow a protocol similar to Prophetic Example 3.

One of skill in the art would also know how to vary a test protocol as described, in order to obtain the best, most accurate, and most reproducible results.

While various embodiments of the present invention have been described above, it should be understood that such disclosures have been presented by way of example only, and are not limiting. Thus, the breadth and scope of the present invention should not be limited by any of the above-described exemplary embodiments, but should be defined only in accordance with the following claims and their equivalents.

Having now fully described the invention, it will be understood by those of ordinary skill in the art that the same can be performed within a wide and equivalent range of conditions, formulations and other parameters without affecting the scope of the invention or any embodiment thereof. All patents, patent applications, and publications cited herein are fully incorporated by reference in their entirety.

What is claimed is:

1. A method of reducing chronic inflammatory pain, acute unresolved pain, pain due to a low threshold of pain, or pain caused by a state of distress in a human subject, wherein the subject has testosterone levels within or below the lower half of the appropriate reference range, comprising:

administering a composition to the human subject, said composition comprising a pain-reducing amount of a testosterone in the absence of exogenous opiates; and wherein pain is reduced safely and effectively.

2. The method of claim 1, wherein the subject's testosterone serum levels are restored from baseline to the middle or upper range of an appropriate reference range.

3. The method of claim 1, wherein the subject is suffering from a condition selected from the group consisting of chronic pain and pain caused by an unresolvable stressor state.

4. The method of claim 3, wherein the unresolvable stressor state is selected from the group consisting of post-traumatic stress disorder (PTSD), accident, trauma, surgery, autoimmune disease, chronic unresolved or acute viral infection, infectious disease, cancer, chronic exhaustion or physical distress, neuropathy, hyperalgesia, allodynia, grief, emotional distress, depression, dysthymia, surgical gonadectomy, and pharmacologic-induced gonadectomy.

5. The method of claim 3, wherein the composition is administered in combination with an antidepressant selected from the group consisting of fluoxetine, duloxetine, sertraline, and a tricyclic antidepressant.

6. The method of claim 3, wherein the subject is a female subject.

7. The method of claim 6, wherein the composition is administered to deliver a daily unit dose of about 1.0 mg to about 12.8 mg of the testosterone, wherein the administration results in steady state total testosterone serum levels without raising free testosterone serum levels or twenty-four hour free testosterone AUC above the levels required for therapeutic efficacy and safety, wherein the administration is selected from the group consisting of transdermal administration, oral administration, parenteral administration, intramuscular administration, and buccal administration.

8. The method of claim 7, wherein the composition is formulated as a gel for transdermal administration, wherein the gel comprises the testosterone and a pharmaceutically acceptable carrier.

9. The method of claim 8, wherein the daily unit dose of the testosterone is from about 2.5 mg to about 10.0 mg.

10. The method of claim 8, wherein the daily unit dose of the testosterone is from about 3.2 mg to about 9.6 mg.

11. The method of claim 10, wherein the daily unit dose of the testosterone is from about 6.0 mg to about 8.0 mg.

12. The method of claim 7, wherein the daily unit dose of the testosterone is selected to maintain steady state total testosterone serum levels within a range of between about 0.9 ng/mL to about 1.4 ng/mL for at least 24 hours after administration.

13. The method of claim 7, wherein free testosterone serum levels and twenty-four hour free testosterone AUC are not raised above levels required for therapeutic efficacy and safety.

14. The method of claim 13, wherein the free testosterone serum levels are raised to about 1.00 pg/mL to about 3.30 pg/mL and the twenty-four hour free testosterone AUC levels are raised to about 40 pg-h/mL to about 65 pg-h/m L.

15. The method of claim 3, wherein the subject is a male subject.

16. The method of claim 15, wherein the testosterone is administered to deliver a daily unit dose of about 35 mg to about 100 mg of the testosterone, wherein the administration results in steady state total testosterone serum levels without raising free testosterone serum levels or twenty-four hour free testosterone AUC above the levels required for therapeutic efficacy and safety, wherein the administration is selected from the group consisting of transdermal administration, oral administration, parenteral administration, intramuscular administration, and buccal administration.

17. The method of claim 16, wherein the composition is formulated as a gel for transdermal administration, wherein the gel comprises the testosterone and at least one pharmaceutically acceptable carrier.

18. The method of claim 16, wherein the daily unit dose of the testosterone is from about 50 mg to about 90 mg/day.

19. The method of claim 18, wherein the daily unit dose of the testosterone is from about 65 mg to about 85 mg.

20. The method of claim 16, wherein the daily unit dose of the testosterone is selected to maintain steady state total testosterone serum levels within a range of between about 2.4 ng/mL to about 9.5 ng/mL for at least 24 hours after administration.

21. The method of claim 16, wherein free testosterone serum levels and twenty-four hour free testosterone AUC are not raised above the levels required for therapeutic efficacy and safety.

22. The method of claim 21, wherein the free testosterone serum levels are raised to about 90 pg/mL to about 300 pg/mL and the twenty-four hour free testosterone AUC levels are raised to about 350 pg-h/mL to about 800 pg-h/mL.

23. The method of claim 22, wherein the free testosterone serum levels are raised to about 150 pg/mL to about 300 pg/mL and the twenty-four hour free testosterone AUC levels are raised to about 400 pg-h/mL to about 700 pg-h/mL.

24. The method of claim 1, wherein the composition consists essentially of the testosterone and at least one pharmaceutically acceptable carrier.

25. A method of increasing the pain threshold of a testosterone-deficient human subject, wherein the human subject suffers from inflammatory pain due to a low threshold of pain resulting from testosterone-deficiency, wherein testosterone levels of the subject are within or below the lower half of the appropriate testosterone reference range, comprising:
administering a composition to the human subject, said composition comprising a pain-threshold increasing amount of testosterone in the absence of exogenous opiates; and
wherein the subject's pain-threshold is increased safely and effectively.

26. The method of claim 25, wherein the subject is suffering from an unresolvable stressor state selected from the group consisting of post-traumatic stress disorder (PTSD), accident, trauma, surgery, autoimmune disease, chronic unresolved or acute viral infection, infectious disease, cancer, chronic exhaustion or physical distress, neuropathy, hyperalgesia, allodynia, grief, emotional distress, depression, dysthymia, surgical gonadectomy, and pharmacologic-induced gonadectomy.

27. The method of claim 25, wherein the subject is a female subject.

28. The method of claim 27, wherein the composition is administered to deliver a daily unit dose of about 1.0 mg to about 12.8 mg of the testosterone, wherein the administration results in steady state total testosterone serum levels without raising free testosterone serum levels or twenty-four hour free testosterone AUC above the levels required for therapeutic efficacy and safety, wherein the administration is selected from the group consisting of transdermal administration, oral administration, parenteral administration, intramuscular administration, and buccal administration.

29. The method of claim 28, wherein the composition is formulated as a gel for transdermal administration, wherein the gel comprises the testosterone and at least one pharmaceutically acceptable carrier.

30. The method of claim 28, wherein the daily unit dose of the testosterone is from about 2.5 mg to about 10.0 mg.

31. The method of claim 30, wherein the daily unit dose of the testosterone is from about 3.2 mg to about 9.6 mg.

32. The method of claim 30, wherein the daily unit dose of the testosterone is from about 6.0 mg to about 8.0 mg.

33. The method of claim 28, wherein the daily unit dose of the testosterone is selected to maintain steady state total testosterone serum levels within a range of between about 0.9 ng/mL to about 1.4 ng/mL for at least 24 hours after administration.

34. The method of claim 33, wherein free testosterone serum levels and twenty-four hour free testosterone AUC are not raised above levels required for therapeutic efficacy and safety.

35. The method of claim 34, wherein the free testosterone serum levels are raised to about 1.00 pg/mL to about 3.30 pg/mL and the twenty-four hour free testosterone AUC levels are raised to about 40 pg-h/mL to about 65 pg-h/mL.

36. The method of claim 25, wherein the subject is a male subject.

37. The method of claim 36, wherein the composition is administered to deliver a daily unit dose of about 35 mg to about 100 mg of the testosterone, wherein the administration results in steady state total testosterone serum levels without raising free testosterone serum levels or twenty-four hour free testosterone AUC above the levels required for therapeutic efficacy and safety, wherein the administration is selected from the group consisting of transdermal administration, oral administration, parenteral administration, intramuscular administration, and buccal administration.

38. The method of claim 37, wherein the composition is formulated as a gel for transdermal administration, wherein the gel comprises the testosterone and a pharmaceutically acceptable carrier.

39. The method of claim 37, wherein the daily unit dose of the testosterone is from about 50 mg to about 90 mg/day.

40. The method of claim 39, wherein the daily unit dose of the testosterone is from about 65 mg to about 85 mg.

41. The method of claim 37, wherein the daily unit dose of the testosterone is selected to maintain steady state total testosterone serum levels within a range of between about 2.4 ng/mL to about 9.5 ng/mL for at least 24 hours after administration.

42. The method of claim 41, wherein free testosterone serum levels and twenty-four hour free testosterone AUC are not raised above the levels required for therapeutic efficacy and safety.

43. The method of claim 42, wherein the free testosterone serum levels are raised to about 90 pg/mL to about 300 pg/mL and the twenty-four hour free testosterone AUC levels are raised to about 350 pg-h/mL to about 800 pg-h/mL.

44. The method of claim 43, wherein the free testosterone serum levels are raised to about 125 pg/mL to about 250 pg/mL and the twenty-four hour free testosterone AUC levels are raised to about 400 pg-h/mL to about 900 pg-h/mL.

45. The method of claim 43 wherein the free testosterone serum levels are raised to about 150 pg/mL to about 300 pg/mL and the twenty-four hour free testosterone AUC levels are raised to about 400 pg-h/mL to about 700 pg-h/mL.

46. The method of claim 25, wherein the composition consists essentially of the testosterone and at least one pharmaceutically acceptable carrier.

47. The method of claim 1, wherein the human subject has at least one of:
   a) elevated C-reactive protein,
   b) elevated erythrocyte sedimentation rate,
   c) DSM-IV disorder 307.80,
   d) DSM-IV disorder 307.89, and
   e) an unresolved stressor state.

48. The method of claim 1, further comprising administering an antidepressant.

49. The method of claim 48, wherein the antidepressant is selected from the group consisting of fluoxetine, duloxetine, sertraline, and a tricyclic antidepressant.

50. A method of reducing chronic inflammatory pain, acute unresolved pain, pain due to a low threshold of pain, or pain caused by a state of distress in a human subject, wherein the subject has testosterone levels within or below the lower half of the appropriate reference range, consisting of:
   administering a composition to the human subject, said composition comprising a pain-reducing amount of testosterone in the absence of exogenous opiates; and
   wherein pain is reduced safely and effectively.

51. The method of claim 50, wherein the human subject has at least one of:
   a) elevated C-reactive protein,
   b) elevated erythrocyte sedimentation rate,
   c) DSM-IV disorder 307.80,
   d) DSM-IV disorder 307.89, and
   e) an unresolved stressor state.

52. A method of reducing chronic inflammatory pain, acute unresolved pain, pain due to a low threshold of pain, or pain caused by a state of distress in a human subject, wherein the subject has testosterone levels within or below the lower half of the appropriate reference range, consisting of:
   administering a composition to the human subject, said composition comprising a pain-reducing amount of testosterone in the absence of exogenous opiates; and
   administering an antidepressant;
   wherein pain is reduced safely and effectively.

53. The method of claim 52, wherein the human subject has at least one of:
   a) elevated C-reactive protein,
   b) elevated erythrocyte sedimentation rate,
   c) DSM-IV disorder 307.80,
   d) DSM-IV disorder 307.89, and
   e) an unresolved stressor state.

54. The method of claim 25, wherein the subject's testosterone serum levels are restored to the middle-upper range of an appropriate reference range.

55. The method of claim 25, wherein the human subject has at least one of:
   a) elevated C-reactive protein,
   b) elevated erythrocyte sedimentation rate,
   c) DSM-IV disorder 307.80,
   d) DSM-IV disorder 307.89, and
   e) an unresolved stressor state.

56. The method of claim 25, further comprising administering an antidepressant.

57. The method of claim 56, wherein the antidepressant is selected from the group consisting of fluoxetine, duloxetine, sertraline, and a tricyclic antidepressant.

58. A method of increasing the pain threshold of a testosterone-deficient human subject, wherein the human subject suffers from inflammatory pain due to a low threshold of pain resulting from testosterone-deficiency, wherein testosterone levels of the subject are within or below the lower half of the appropriate testosterone reference range, consisting of:
   administering a composition to the human subject, said composition comprising a pain-threshold increasing amount of testosterone in the absence of exogenous opiates; and
   wherein the subject's pain-threshold is increased safely and effectively.

59. The method of claim 58, wherein the human subject has at least one of:
   a) elevated C-reactive protein,
   b) elevated erythrocyte sedimentation rate,
   c) DSM-IV disorder 307.80,
   d) DSM-IV disorder 307.89, and
   e) an unresolved stressor state.

60. A method of increasing the pain threshold of a testosterone-deficient human subject, wherein the human subject suffers from inflammatory pain due to a low threshold of pain resulting from testosterone-deficiency, wherein testosterone levels of the subject are within or below the lower half of the appropriate testosterone reference range, consisting of:
   administering a composition to the human subject, said composition comprising a pain-threshold increasing amount of testosterone in the absence of exogenous opiates; and
   administering an antidepressant;
   wherein the subject's pain-threshold is increased safely and effectively.

61. The method of claim 60, wherein the human subject has at least one of:
   a) elevated C-reactive protein,
   b) elevated erythrocyte sedimentation rate,
   c) DSM-IV disorder 307.80,
   d) DSM-IV disorder 307.89, and
   e) an unresolved stressor state.

* * * * *